United States Patent [19]

Takemoto et al.

[11] 4,309,212
[45] Jan. 5, 1982

[54] HERBICIDAL COMPOSITIONS AND METHODS EMPLOYING UREA DERIVATIVES

[75] Inventors: Ichiki Takemoto, Takarazuka; Seizo Sumida, Nishinomiya; Ryo Yoshida, Kawanishi; Katsuzo Kamoshita, Osaka, all of Japan

[73] Assignee: Sumitomo Chemical Company, Limited, Osaka, Japan

[21] Appl. No.: 952,775

[22] Filed: Oct. 19, 1978

[30] Foreign Application Priority Data

Oct. 26, 1977 [JP] Japan .................. 52-129089
Feb. 28, 1978 [JP] Japan .................. 53-23027
Mar. 1, 1978 [JP] Japan .................. 53-23891

[51] Int. Cl.³ .............................. A01N 47/30
[52] U.S. Cl. .................. 71/120; 424/322; 260/453 RW; 564/49; 564/52
[58] Field of Search ............................. 71/120

[56] References Cited
U.S. PATENT DOCUMENTS 3,819,697  6/1974  Cross .................. 260/553 A
4,129,436 12/1978  Takemoto et al. .................. 71/120

*Primary Examiner*—Catherine L. Mills
*Attorney, Agent, or Firm*—Birch, Stewart, Kolasch & Birch

[57] ABSTRACT

Novel N'-phenyl-N-methylurea derivatives of the formula:

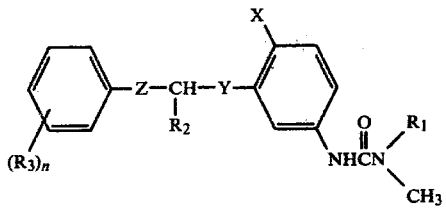

wherein $R_1$ is a hydrogen atom, a methyl group or a methoxy group, $R_2$ is a hydrogen atom or a lower alkyl group, $R_3$, which may be the same or different, is a halogen atom, a lower alkyl group, a lower alkoxy group, a lower alkylthio group or a trifluoromethyl group, n is an integer of 0 to 5, X is a hydrogen atom or a halogen atom, Y is an oxygen atom or a sulfur atom and Z is a straight or branched $C_1$–$C_8$ alkylene group which may have no less than one atom of oxygen and/or sulfur at the terminal of and/or inside the carbon chain, which shows a pronounced herbicidal activity against a wide variety of weeds in the cultivation of crop plants as well as a notable fungicidal activity against a wide variety of phytopathogenic fungi causing plant diseases to crop plants without any material toxicity to mammals and fish or any chemical injury to said crop plants.

11 Claims, No Drawings

HERBICIDAL COMPOSITIONS AND METHODS EMPLOYING UREA DERIVATIVES

The present invention relates to N'-phenyl-N-methylurea derivatives of the formula (I):

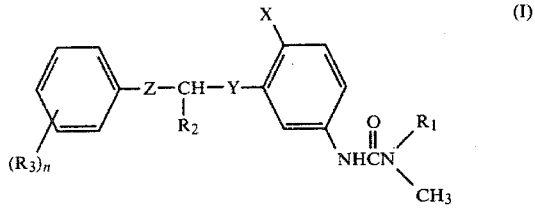

wherein $R_1$ is a hydrogen atom, a methyl group or a methoxy group, $R_2$ is a hydrogen atom or a lower alkyl group, $R_3$, which may be the same or different, is a halogen atom, a lower alkyl group, a lower alkoxy group, a lower alkylthio group or a trifluoromethyl group, n is an integer of 0 to 5, X is a hydrogen atom or a halogen atom, Y is an oxygen atom or a sulfur atom and Z is a straight or branched $C_1$-$C_8$ alkylene group which may have no less than one atom of oxygen and/or sulfur inside and/or at the end of the alkylene chain, and their production and use.

In the formula (I), $R_2$ includes, for example, hydrogen, methyl and ethyl; $R_3$ includes, for example, methyl, ethyl, propyl, butyl, fluorine, chlorine, bromine, methoxy, ethoxy, propoxy, butoxy, methylthio, ethylthio, propylthio, butylthio and trifluoromethyl; X includes, for example, hydrogen, fluorine, chlorine and bromine; and Z includes, for example, ethylene, ethylidene, trimethylene, 2-methylethylene, 1-methylethylene, tetramethylene, 1-methyltrimethylene, 1,2-dimethylethylene, 2,2-dimethylethylene, pentamethylene, 2-methyltetramethylene, 3-methyltetramethylene, 2,3-dimethyltrimethylene, 2,2-dimethyltrimethylene, 3-ethyltrimethylene, hexamethylene, 5-methylpentamethylene, 2,4-dimethyltetramethylene, 3-ethyltetramethylene, 2,3,3-trimethyltrimethylene, 3-propyltrimethylene, heptamethylene, 2-methylhexamethylene, 4-methylhexamethylene, 5-methylhexamethylene, 2,5-dimethylpentamethylene, 3,5-dimethylpentamethylene, 5,5-dimethylpentamethylene, 4-ethylpentamethylene, 2,3,4-trimethyltetramethylene, 2,4,4-trimethyltetramethylene, 2-propyltetramethylene, octamethylene, 6-methylheptamethylene, 4,6-dimethylhexamethylene, 4-ethylhexamethylene, 2,4,5-trimethylpentamethylene, 2-methyl-5-ethylpentamethylene, methyleneoxy, methylenethio, 2-oxaethylene, 2-thiaethylene, 1-ethyl-2-oxaethylene, 3-oxatrimethylene, 3-thiatrimethylene, 1-oxatrimethylene, 2-oxatrimethylene, 2-thiatrimethylene, 4-oxatetramethylene, 4-thiatetramethylene, 1-methyl-3-oxatrimethylene, 3-oxatetramethylene, 2,5-dioxapentamethylene, 5-thia-2-oxapentamethylene, 5-oxapentamethylene, 1-methyl-4-oxatetramethylene, 1-ethyl-3-oxatrimethylene, 4-thiapentamethylene, 2,5-dioxahexamethylene, 6-oxahexamethylene, 6-thiahexamethylene, 1,3-dimethyl-4-oxatetramethylene, 2,6-dioxahexamethylene, 2,6-dithiahexamethylene, 4-oxahexamethylene, 3-ethyl-4-oxapentamethylene, 2,5,8-trioxaoctamethylene, 7-oxaheptamethylene, 4-oxaheptamethylene, 8-oxaoctamethylene and 8-thiaoctamethylene (the numeral indicating the position numbered from the side of the phenylurea moiety).

Rice, wheat, corn, soybean, cotton, sugarbeet and the like are important crops, and the use of herbicides is essential to protect these crops from damage by weeds and to increase the yield thereof. For the purpose of finding herbicides having high selectivity to these crop plants and strong herbicidal activity against weeds with low toxicity to mammals, a study has been made by the present inventors.

Among urea series compounds, as is well known, there are compounds such as N'-4-chlorophenyl-N,N-dimethylurea (monuron) and N'-3,4-dichlorophenyl-N,N-dimethylurea (diuron), which have a strong herbicidal activity. Further, it is well known that the herbicidal activity of these urea compounds is due to their inhibitory action against photosynthesis. Photosynthesis is a physiological function peculiar to higher plants and is not operative in mammals. Accordingly, it is highly possible that specific inhibitors of photosynthetic processes do not do significant damage to mammals but can exterminate higher plants. In fact, photosynthesis inhibitors such as N'-4-chlorophenyl-N,N-dimethylurea, N'-3,4-dichlorophenyl-N,N-dimethylurea, 5-bromo-3-sec-butyluracil (bromacil) and the like are all low in mammalian toxicity. As stated above, the photosynthesis inhibitors have the merit that they are generally low in mammalian toxicity, but they have a possibility of exerting herbicidal activity on every higher plant since photosynthesis is common to all higher plants. As it is, most photosynthesis inhibitors are non-selective and do damage to crop plants. Thus, it is necessary for selective herbicides to have a strong herbicidal activity against weeds alone without inflicting damage on the intended crop plants. But selective herbicides having both a high selectivity and a strong herbicidal activity are very difficult to find and can not easily be thought out systematically by mere analogy and modification of known chemical structures. Therefore, a highly detailed study with trial and error is necessary to find such selective herbicides. For example, N'-3,4-dichlorophenyl-N-methoxy-N-methylurea (linuron) among urea series compounds has selectivity to Umbelliferae family plants, but compounds having a methyl or ethyl group in place of the methoxy group of linuron lose the selectivity to the same plants completely [Herbicide Handbook of The Weed Science Society of America, 3rd Ed., pages 172–176 and 221–225 (1974)]. As described above, the mechanism of the selective herbicidal activity is very specific, and a slight difference in chemical structure results in a large difference in degree and kind of selectivity.

Attention was paid in this study to urea series compounds from the standpoints of low toxicity to mammals and strong herbicidal activity, and an attempt was made to produce derivatives improved in selectivity. As a result, it has been found that the compounds of the formula (I) exhibit a strong herbicidal activity against many weeds by inhibition of photosynthesis, and, in addition, have high selectivity, depending on their kinds, to various important crop plants.

Referring to the herbicidal activity of the compounds (I) in more detail, they have a strong herbicidal activity against a wide range of paddy field weeds by either pre-emergence treatment or post-emergence treatment. For example, they have a strong herbicidal activity against paddy field weeds such as tooth cup (*Rotala indica*), water starwort (*Callitriche verna*), false pimpernel (*Linderna pyxidaria*), pickerel weed (*Monochoria vaginalis*), *Dopatrium junceum*, *Vandellia angustifolia*

Benth., barnyard grass (*Echinochloa crus-galli*), nutsedge sp. (*Cyperus difformis*) and the like. But they have high selectivity to rice plants as described above. Also, the compounds (I) have strong herbicidal activity against a wide range of upland field weeds when applied by post-emergence treatment. The field weeds include, for example, broad-leaved weeds such as cocklebur (*Xanthium pennsylvanicum*), sunflower (*Helianthus annuus*), redroot pigweed (*Amaranthus retroflexus*), common lambsquarters (*Chenopodium album*), annual morningglory (*Ipomoea purpurea*), jimsonweed (*Datura stramonium*), black nightshade (*Solanum nigrum*), prickly sida (*Sida spinosa*), sicklepod (*Cassia obtusifolia*), common purslane (*Portulaca oleracea*), smartweed sp. (*Poligonum sp.*), giant ragweed (*Ambrosia trifida*), velvetleaf (*Abutilon theophrasti*), shepherd's-purse (*Capsella bursa-pastoris*), bitter cress sp. (*Cardamine flexuosa*), chickweed (*Stellaria media*), catchweed bedstraw (*Galium aparine L.*), mouseear chickweed (*Cerastium glomerastum*), *Sagina japonica* Ohwi, johnson grass (*Sorghum halepense*), sesbania (*Sesbania spp.*) and the like; and grassy weeds such as barnyard grass (Echinochloa crusgalli), large crabgrass (*Digitaria sanguinalis*), green foxtail (*Setaria viridis*), annual bluegrass (*Poa annua*), wild oat (*Avena fatua L.*) and the like. As described hereinafter, the compounds (I) have high selectivity to soybean, cotton, sugarbeet, corn and wheat.

The compounds of the formula (I) are novel, and N'-(3-benzyloxyphenyl)-N,N-dimethylurea in U.S. Pat. No. 3,819,697 (hereinafter referred to as "control compound (a)") is known to be similar in chemical structure to them. But the herbicidal activity of the compounds (I) is extremely stronger than that of the control compound (a), as is shown in the examples. That is to say, the herbicidal activity is remarkably improved by lengthening the —CH$_2$— chain of the benzyl group in the control compound (a), in other words, by replacing the benzyl group by a phenyl-(C$_2$–C$_9$)alkyl group such as phenethyl, phenylpropyl, phenylbutyl or phenylnonyl, or an oxygen- or sulfur-containing phenyl(C$_2$–C$_8$)alkyl group such as phenoxyethyl, phenylthioethyl or phenoxypropyl.

Further, the following unexpected fact was found: the selectivity and/or herbicidal activity of the compounds (I) can be enhanced by introducing a substituent into the benzene ring.

As stated above, it is clear that the compounds (I) of the present invention are very effective as selective herbicides for agricultural lands. Also, they are excellent herbicides which can be applied in non-crop lands because of their strong herbicidal activity.

In addition, it may be noted that the compounds (I) of the invention are effective in prevention and inhibition of plant diseases caused by various phytopathogenic fungi in crop plants and fruit trees such as powdery mildew in apples, grapes, oranges, cucumbers, melons, wheats, etc., downy mildew in grapes, oranges, cucumbers, melons, etc., yellows in root crops and rust in wheats, beans, etc. They are particularly effective in prevention and inhibition of rust such as stripe rust in barleys and wheats caused by *Puccinia striiformis*, stem rust in barleys and wheats caused by *Puccinia graminis*, leaf rust in wheats caused by *Puccinia recondita*, crown rust in oats caused by *Puccinia coronata*, rust in soybeans caused by *Uromyces sojae*, rust in kidney beans caused by *Uromyces appendiculatus* and rust in coffee caused by *Hemileia vastatrix*. Compared with conventional fungicides, the compounds (I) are characteristic in having not only a preventive effect but also a curative effect.

Accordingly, the compounds (I) of the present invention are useful as fungicides. Particularly when they are used in cultivation of paddy rice plants, upland rice plants, cotton, soybeans, corn, wheat, barleys, etc., the simutaneous production of a herbicidal action and a fungicidal action can be expected.

The compounds (I) can be produced by the following methods:

(a) A process comprising reacting a phenylisocyanate derivative of the formula (II):

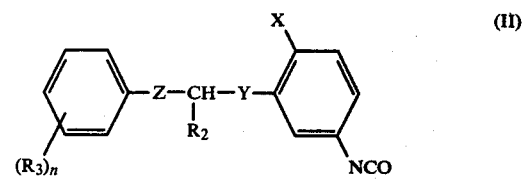

wherein R$_2$, R$_3$, n, X, Y and Z are each as defined above, with monomethylamine, dimethylamine or N,O-dimethylhydroxylamine.

This reaction may be carried out in an organic solvent (e.g. benzene, toluene, xylene, diethyl ether, tetrahydrofuran, dioxane, N,N-dimethylformamide, chloroform, carbon tetrachloride), water or a mixture thereof. The reaction is usually effected at a temperature of 0° to 50° C. in 1 to 10 hours, whereby the objective compound can be obtained in a high yield.

(b) A process comprising methylating an N'-phenyl-N-hydroxyurea derivative of the formula (III):

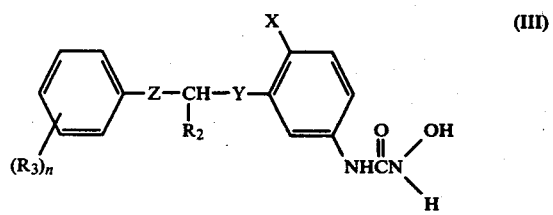

wherein R$_2$, R$_3$, n, X, Y and Z are each as defined above.

As the methylating agent, there may be used, for example, methyl iodide, dimethyl sulfate or diazomethane. When dimethyl sulfate is used, for example, the reaction can be carried out in a solvent in the presence of an alkali. The alkali includes sodium hydroxide and potassium hydroxide, and the solvent includes organic solvents (e.g. benzene, toluene, xylene, methanol, ethanol, isopropanol, diethyl ether, tetrahydrofuran, dioxane, methylene chloride), water and a mixture thereof. The existence of a phase transfer catalyst such as benzyltriethylammonium chloride or tetra-n-butylammonium bromide is advantageous in the reaction. The reaction is usually effected at a temperature of 0° to 100° C. in 1 to 10 hours, whereby the objective compound can be obtained in a high yield.

(c) A process comprising reacting an aniline derivative of the formula (IV):

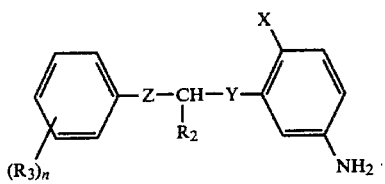

(IV)

wherein $R_2$, $R_3$, n, X, Y and Z are each as defined above, with methyl isocyanate, N-methoxy-N-methylcarbamyl chloride. or N,N-dimethylcarbamyl chloride.

This reaction is carried out in an organic solvent (e.g. benzene, toluene, xylene, diethyl ether, tetrahydrofuran, dioxane, chloroform, carbon tetrachloride, ethyl acetate, pyridine, dimethylformamide). The yield of the reaction can be increased by using a dehydrochlorinating agent such as pyridine, triethylamine, sodium hydroxide and potassium hydroxide. The reaction is usually effected at a temperature of 0° to 150° C. in 1 to 10 hours whereby the objective compound can be obtained in a high yield.

(d) A process comprising reacting a halide of the formula (V):

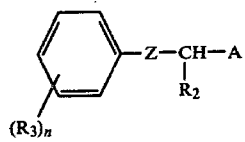

(V)

wherein $R_2$, $R_3$, n and Z are each as defined above and A is a halogen atom, with an N'-phenyl-N-methylurea derivative of the formula (VI):

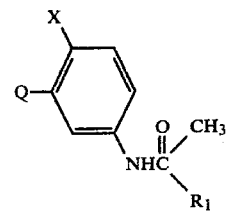

(VI)

wherein $R_1$ and X are each as defined above and Q is a hydroxyl group or a mercapto group.

This reaction is carried out in a solvent in the presence of a dehydrohalogenating agent. Examples of the dehydrohalogenating agent include pyridine, triethylamine, sodium hydroxide, potassium hydroxide, sodium carbonate, etc. Examples of the solvent are organic solvents (e.g. benzene, toluene, xylene, diethyl ether, tetrahydrofuran, dioxane, chloroform, carbon tetrachloride, methylene chloride, ethyl acetate, methanol, ethanol, isopropanol, N,N-dimethylformamide), water and mixtures thereof.

The phenylisocyanate derivative of the formula (II) in the process (a) can easily be obtained by reaction between the aniline derivative of the formula (IV) and phosgene. The N'-phenyl-N-hydroxyurea derivative of the formula (III) in the process (b) can easily be obtained by reaction between the phenylisocyanate derivative of the formula (II) (obtained by reaction between the corresponding aniline derivative of the formula (IV) and phosgene) and hydroxylamine.

Some examples of the compounds of the formula (I) will be shown below but the compounds of the invention are not limited to these examples.

| Compound No. | Chemical structure | Melting point or refractive index |
|---|---|---|
| 1 | ⟨⟩—CH₂CH₂O—⟨⟩—NHC(O)N(OCH₃)(CH₃) | M.P., 82.0–82.5° C. |
| 2 | ⟨⟩—CH₂CH₂O—⟨⟩—NHC(O)N(CH₃)(CH₃) | M.P., 100–101° C. |
| 3 | 2-CH₃-⟨⟩—CH₂CH₂O—⟨⟩—NHC(O)N(OCH₃)(CH₃) | M.P., 88–89° C. |
| 4 | 2-CH₃-⟨⟩—CH₂CH₂O—⟨⟩—NHC(O)N(CH₃)(CH₃) | M.P., 106–107° C. |

-continued

| Compound No. | Chemical structure | Melting point or refractive index |
|---|---|---|
| 5 | 2-($C_2H_5$)-C_6H_4-CH_2CH_2O-C_6H_4-NHC(=O)N(OCH_3)(CH_3) | $n_D^{24.5}$ 1.6715 |
| 6 | 2-($C_2H_5$)-C_6H_4-CH_2CH_2O-C_6H_4-NHC(=O)N(CH_3)(CH_3) | M.P., 65–66° C. |
| 7 | 2-($OCH_3$)-C_6H_4-CH_2CH_2O-C_6H_4-NHC(=O)N(OCH_3)(CH_3) | M.P., 85–86° C. |
| 8 | 2-($OCH_3$)-C_6H_4-CH_2CH_2O-C_6H_4-NHC(=O)N(CH_3)(CH_3) | M.P., 83–84° C. |
| 9 | 3-($H_3C$)-C_6H_4-CH_2CH_2O-C_6H_4-NHC(=O)N(OCH_3)(CH_3) | M.P., 92.0–92.5° C. |
| 10 | 3-($H_3C$)-C_6H_4-CH_2CH_2O-C_6H_4-NHC(=O)N(CH_3)(CH_3) | M.P., 71–72° C. |
| 11 | 3-($H_3CO$)-C_6H_4-CH_2CH_2O-C_6H_4-NHC(=O)N(OCH_3)(CH_3) | M.P., 53–54° C. |
| 12 | 3-($H_3CO$)-C_6H_4-CH_2CH_2O-C_6H_4-NHC(=O)N(CH_3)(CH_3) | M.P., 118–119° C. |
| 13 | 4-($H_3C$)-C_6H_4-CH_2CH_2O-C_6H_4-NHC(=O)N(OCH_3)(CH_3) | M.P., 99–100° C. |
| 14 | 4-($H_3C$)-C_6H_4-CH_2CH_2O-C_6H_4-NHC(=O)N(CH_3)(CH_3) | M.P., 126–127° C. |

-continued

| Compound No. | Chemical structure | Melting point or refractive index |
|---|---|---|
| 15 | i-H$_7$C$_3$—⟨C$_6$H$_4$⟩—CH$_2$CH$_2$O—⟨C$_6$H$_4$⟩—NHC(=O)N(OCH$_3$)(CH$_3$) | $n_D^{26}$ 1.5610 |
| 16 | i-H$_7$C$_3$—⟨C$_6$H$_4$⟩—CH$_2$CH$_2$O—⟨C$_6$H$_4$⟩—NHC(=O)N(CH$_3$)(CH$_3$) | M.P., 68–69° C. |
| 17 | t-H$_9$C$_4$—⟨C$_6$H$_4$⟩—CH$_2$CH$_2$O—⟨C$_6$H$_4$⟩—NHC(=O)N(OCH$_3$)(CH$_3$) | M.P., 91–92° C. |
| 18 | t-H$_9$C$_4$—⟨C$_6$H$_4$⟩—CH$_2$CH$_2$O—⟨C$_6$H$_4$⟩—NHC(=O)N(CH$_3$)(CH$_3$) | M.P., 130–131° C. |
| 19 | H$_3$CO—⟨C$_6$H$_4$⟩—CH$_2$CH$_2$O—⟨C$_6$H$_4$⟩—NHC(=O)N(OCH$_3$)(CH$_3$) | M.P., 74–75° C. |
| 20 | H$_3$CO—⟨C$_6$H$_4$⟩—CH$_2$CH$_2$O—⟨C$_6$H$_4$⟩—NHC(=O)N(CH$_3$)(CH$_3$) | M.P., 108–109° C. |
| 21 | F—⟨C$_6$H$_4$⟩—CH$_2$CH$_2$O—⟨C$_6$H$_4$⟩—NHC(=O)N(OCH$_3$)(CH$_3$) | M.P., 78–79° C. |
| 22 | F—⟨C$_6$H$_4$⟩—CH$_2$CH$_2$O—⟨C$_6$H$_4$⟩—NHC(=O)N(CH$_3$)(CH$_3$) | M.P., 125–126° C. |
| 23 | Cl—⟨C$_6$H$_4$⟩—CH$_2$CH$_2$O—⟨C$_6$H$_4$⟩—NHC(=O)N(OCH$_3$)(CH$_3$) | M.P., 86–87° C. |
| 24 | Cl—⟨C$_6$H$_4$⟩—CH$_2$CH$_2$O—⟨C$_6$H$_4$⟩—NHC(=O)N(CH$_3$)(CH$_3$) | M.P., 153–154° C. |
| 25 | 2,4-(CH$_3$)$_2$-⟨C$_6$H$_3$⟩—CH$_2$CH$_2$O—⟨C$_6$H$_4$⟩—NHC(=O)N(OCH$_3$)(CH$_3$) | $n_D^{28.5}$ 1.5561 |

| Compound No. | Chemical structure | Melting point or refractive index |
|---|---|---|
| 26 | 2,4-(CH₃)₂C₆H₃-CH₂CH₂O-C₆H₄-NHC(=O)N(CH₃)(CH₃) | M.P., 142–143.5° C. |
| 27 | 2,4-(CH₃)₂C₆H₃-CH₂CH₂O-C₆H₄-NHC(=O)N(OCH₃)(CH₃) | M.P., 49–50° C. |
| 28 | 2,4-(CH₃)₂C₆H₃-CH₂CH₂O-C₆H₄-NHC(=O)N(CH₃)(CH₃) | M.P., 94–95° C. |
| 29 | 4-Br-C₆H₄-CH₂CH₂O-C₆H₄-NHC(=O)N(OCH₃)(CH₃) | M.P., 95–98° C. |
| 30 | 2-Cl-C₆H₄-CH₂CH₂O-C₆H₄-NHC(=O)N(OCH₃)(CH₃) | M.P., 74–75° C. |
| 31 | 2-Cl-C₆H₄-CH₂CH₂O-C₆H₄-NHC(=O)N(CH₃)(CH₃) | M.P., 93–94° C. |
| 32 | C₆H₅-CH₂CH₂O-C₆H₄-NHC(=O)N(CH₃)(H) | M.P., 98–99° C. |
| 33 | 4-Cl-C₆H₄-CH₂CH₂O-C₆H₄-NHC(=O)N(CH₃)(H) | M.P., 126–127° C. |
| 34 | C₆H₅-CH₂CH₂S-C₆H₄-NHC(=O)N(OCH₃)(CH₃) | m.P., 76–77° C. |
| 35 | C₆H₅-CH₂CH₂S-C₆H₄-NHC(=O)N(CH₃)(CH₃) | M.P., 100–100.5° C. |

-continued

| Compound No. | Chemical structure | Melting point or refractive index |
|---|---|---|
| 36 | C6H5-CH2CH2S-C6H4-NHC(O)N(CH3)(H) | M.P., 85–86° C. |
| 37 | 2-CH3-C6H4-CH2CH2S-C6H4-NHC(O)N(OCH3)(CH3) | M.P., 99–100° C. |
| 38 | 2-CH3-C6H4-CH2CH2S-C6H4-NHC(O)N(CH3)(CH3) | M.P., 128–129° C. |
| 39 | 3-H3CO-C6H4-CH2CH2S-C6H4-NHC(O)N(OCH3)(CH3) | M.P., 64–65° C. |
| 40 | 3-H3CO-C6H4-CH2CH2S-C6H4-NHC(O)N(CH3)(CH3) | M.P., 92–93° C. |
| 41 | sec-H9C4-C6H4-CH2CH2S-C6H4-NHC(O)N(OCH3)(CH3) | $n_D^{23.5}$ 1.5792 |
| 42 | sec-H9C4-C6H4-CH2CH2S-C6H4-NHC(O)N(CH3)(CH3) | M.P., 57–58° C. |
| 43 | 4-F-C6H4-CH2CH2S-C6H4-NHC(O)N(OCH3)(CH3) | M.P., 84–85° C. |
| 44 | 4-F-C6H4-CH2CH2S-C6H4-NHC(O)N(CH3)(CH3) | M.P., 95–96° C. |
| 45 | 4-Cl-C6H4-CH2CH2S-C6H4-NHC(O)N(OCH3)(CH3) | M.P., 88–89° C. |
| 46 | 4-Cl-C6H4-CH2CH2S-C6H4-NHC(O)N(CH3)(CH3) | M.P., 108–109° C. |

-continued
| Compound No. | Chemical structure | Melting point or refractive index |
|---|---|---|
| 47 | 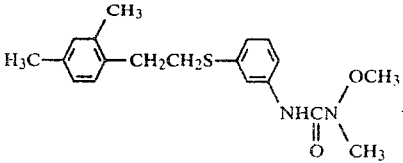 | M.P., 63–64° C. |
| 48 | 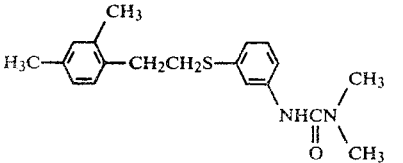 | M.P., 103–104° C. |
| 49 | 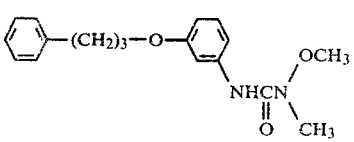 | M.P., 82–83° C. |
| 50 | 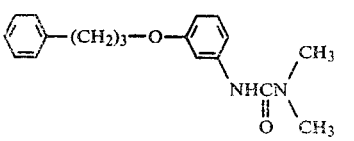 | M.P., 130–131.5° C. |
| 51 | 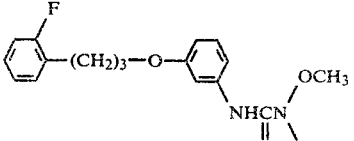 | M.P., 93–95° C. |
| 52 | 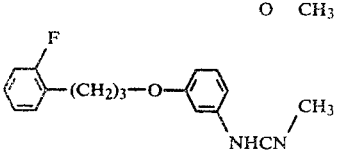 | M.P., 126–127° C. |
| 53 | 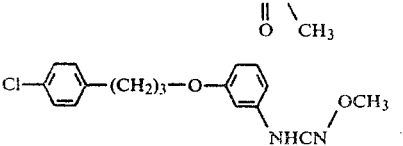 | M.P., 78–79° C. |
| 54 | 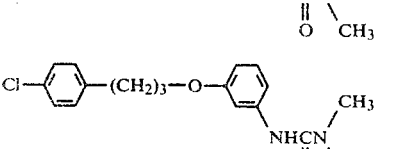 | M.P., 149.5–151° C. |
| 55 | 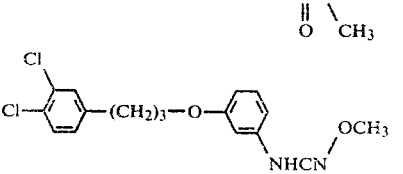 | M.P., 68–69° C. |
| 56 | 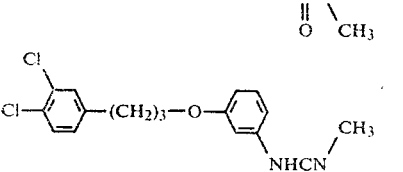 | M.P., 127–128° C. |

-continued

| Compound No. | Chemical structure | Melting point or refractive index |
|---|---|---|
| 57 | H₃C—⟨⟩—(CH₂)₃—O—⟨⟩—NHC(=O)N(OCH₃)(CH₃) | M.P., 75–76° C. |
| 58 | H₃C—⟨⟩—(CH₂)₃—O—⟨⟩—NHC(=O)N(CH₃)(CH₃) | M.P., 110–111° C. |
| 59 | t-H₉C₄—⟨⟩—(CH₂)₃—O—⟨⟩—NHC(=O)N(OCH₃)(CH₃) | M.P., 85–86° C. |
| 60 | t-H₉C₄—⟨⟩—(CH₂)₃—O—⟨⟩—NHC(=O)N(CH₃)(CH₃) | M.P., 118–119° C. |
| 61 | 2,4-(CH₃)₂-C₆H₃—(CH₂)₃—O—⟨⟩—NHC(=O)N(OCH₃)(CH₃) | $n_D^{25}$ 1.5621 |
| 62 | 2,4-(CH₃)₂-C₆H₃—(CH₂)₃—O—⟨⟩—NHC(=O)N(CH₃)(CH₃) | M.P., 89–91° C. |
| 63 | H₃C—⟨⟩—CH(CH₃)CH₂—O—⟨⟩—NHC(=O)N(OCH₃)(CH₃) | M.P., 81–82° C. |
| 64 | H₃C—⟨⟩—CH(CH₃)CH₂—O—⟨⟩—NHC(=O)N(CH₃)(CH₃) | M.P., 109–111° C. |
| 65 | C₆H₅—(CH₂)₄—O—⟨⟩—NHC(=O)N(OCH₃)(CH₃) | M.P., 72.5–73.5° C. |
| 66 | C₆H₅—(CH₂)₄—O—⟨⟩—NHC(=O)N(CH₃)(CH₃) | M.P., 115–116° C. |
| 67 | H₃C—⟨⟩—(CH₂)₄—O—⟨⟩—NHC(=O)N(OCH₃)(CH₃) | M.P., 80–81° C. |

-continued

| Compound No. | Chemical structure | Melting point or refractive index |
|---|---|---|
| 68 | H$_3$C—⟨C$_6$H$_4$⟩—(CH$_2$)$_4$—O—⟨C$_6$H$_4$⟩—NHC(=O)N(CH$_3$)(CH$_3$) | M.P., 147–148° C. |
| 69 | ⟨C$_6$H$_5$⟩—CH(CH$_3$)(CH$_2$)$_2$—O—⟨C$_6$H$_4$⟩—NHC(=O)N(OCH$_3$)(CH$_3$) | $n_D^{24.5}$ 1.5545 |
| 70 | ⟨C$_6$H$_5$⟩—CH(CH$_3$)(CH$_2$)$_2$—O—⟨C$_6$H$_4$⟩—NHC(=O)N(CH$_3$)(CH$_3$) | M.P., 81–82° C. |
| 71 | H$_3$CO—⟨C$_6$H$_4$⟩—(CH$_2$)$_4$—S—⟨C$_6$H$_4$⟩—NHC(=O)N(OCH$_3$)(CH$_3$) | M.P., 62–63° C. |
| 72 | H$_3$CO—⟨C$_6$H$_4$⟩—(CH$_2$)$_4$—S—⟨C$_6$H$_4$⟩—NHC(=O)N(CH$_3$)(CH$_3$) | M.P., 120–121.5° C. |
| 73 | ⟨C$_6$H$_5$⟩—(CH$_2$)$_5$—O—⟨C$_6$H$_4$⟩—NHC(=O)N(OCH$_3$)(CH$_3$) | M.P., 47–48° C. |
| 74 | ⟨C$_6$H$_5$⟩—(CH$_2$)$_5$—O—⟨C$_6$H$_4$⟩—NHC(=O)N(CH$_3$)(CH$_3$) | M.P., 117–118° C. |
| 75 | ⟨C$_6$H$_5$⟩—CH(C$_2$H$_5$)CH$_2$CH$_2$—O—⟨C$_6$H$_4$⟩—NHC(=O)N(OCH$_3$)(CH$_3$) | $n_D^{25}$ 1.5565 |
| 76 | ⟨C$_6$H$_5$⟩—CH(C$_2$H$_5$)CH$_2$CH$_2$—O—⟨C$_6$H$_4$⟩—NHC(=O)N(CH$_3$)(CH$_3$) | M.P., 98–100° C. |
| 77 | ⟨C$_6$H$_5$⟩—(CH$_2$)$_5$—S—⟨C$_6$H$_4$⟩—NHC(=O)N(OCH$_3$)(CH$_3$) | $n_D^{25.5}$ 1.5870 |
| 78 | ⟨C$_6$H$_5$⟩—(CH$_2$)$_5$—S—⟨C$_6$H$_4$⟩—NHC(=O)N(CH$_3$)(CH$_3$) | M.P., 191–192.5° C. |

-continued

| Compound No. | Chemical structure | Melting point or refractive index |
|---|---|---|
| 79 | H₃C–C₆H₄–CHCH–CH(CH₃)–CH₂–O–C₆H₄–NHC(O)N(OCH₃)(CH₃), with CH₃ branch | $n_D^{25}$ 1.4560 |
| 80 | H₃C–C₆H₄–CHCH–CH(CH₃)–CH₂–O–C₆H₄–NHC(O)N(CH₃)₂, with CH₃ branch | M.P., 115–116° C. |
| 81 | C₆H₅–(CH₂)₇–O–C₆H₄–NHC(O)N(OCH₃)(CH₃) | M.P., 33–35° C. |
| 82 | C₆H₅–(CH₂)₇–O–C₆H₄–NHC(O)N(CH₃)₂ | M.P., 97–98° C. |
| 83 | C₆H₅–(CH₂)₉–O–C₆H₄–NHC(O)N(OCH₃)(CH₃) | M.P., 45–46° C. |
| 84 | C₆H₅–(CH₂)₉–O–C₆H₄–NHC(O)N(CH₃)₂ | M.P., 78–80° C. |
| 85 | 2-CH₃–C₆H₄–(CH₂)₉–O–C₆H₄–NHC(O)N(OCH₃)(CH₃) | $n_D^{25.5}$ 1.5410 |
| 86 | 2-CH₃–C₆H₄–(CH₂)₉–O–C₆H₄–NHC(O)N(CH₃)₂ | M.P., 69–70° C. |
| 87 | C₆H₅–OCH₂CH₂–O–C₆H₄–NHC(O)N(OCH₃)(CH₃) | M.P., 129–130° C. |
| 88 | C₆H₅–OCH₂CH₂–O–C₆H₄–NHC(O)N(CH₃)₂ | M.P., 170–172° C. |
| 89 | 3-F₃C–C₆H₄–OCH₂CH₂–O–C₆H₄–NHC(O)N(OCH₃)(CH₃) | M.P., 106–107° C. |

| Compound No. | Chemical structure | Melting point or refractive index |
|---|---|---|
| 90 | F₃C-C₆H₃-OCH₂CH₂-O-C₆H₄-NHC(O)N(CH₃)CH₃ | M.P., 152–153° C. |
| 91 | H₃C-C₆H₄-OCH₂CH₂-O-C₆H₄-NHC(O)N(OCH₃)CH₃ | M.P., 103–104° C. |
| 92 | H₃C-C₆H₄-OCH₂CH₂-O-C₆H₄-NHC(O)N(CH₃)CH₃ | M.P., 148–149° C. |
| 93 | 2,4-Cl₂-C₆H₃-OCH₂CH₂-O-C₆H₄-NHC(O)N(OCH₃)CH₃ | M.P., 127–128° C. |
| 94 | 2,4-Cl₂-C₆H₃-OCH₂CH₂-O-C₆H₄-NHC(O)N(CH₃)CH₃ | M.P., 167–168° C. |
| 95 | 4-Cl-2,5-(CH₃)₂-C₆H₂-OCH₂CH₂-O-C₆H₄-NHC(O)N(OCH₃)CH₃ | M.P., 99–100° C. |
| 96 | 4-Cl-2,5-(CH₃)₂-C₆H₂-OCH₂CH₂-O-C₆H₄-NHC(O)N(CH₃)CH₃ | M.P., 125–126° C. |
| 97 | C₆F₅-OCH₂CH₂-O-C₆H₄-NHC(O)N(OCH₃)CH₃ | M.P., 64–65° C. |
| 98 | C₆F₅-OCH₂CH₂-O-C₆H₄-NHC(O)N(CH₃)CH₃ | M.P., 114–115° C. |
| 99 | C₆H₅-SCH₂CH₂-O-C₆H₄-NHC(O)N(OCH₃)CH₃ | M.P., 65–66° C. |

-continued

| Compound No. | Chemical structure | Melting point or refractive index |
|---|---|---|
| 100 | C₆H₅—SCH₂CH₂—O—C₆H₄—NHC(=O)N(CH₃)₂ | M.P., 126–127.5° C. |
| 101 | H₃C—C₆H₄—O(CH₂)₃—O—C₆H₄—NHC(=O)N(OCH₃)(CH₃) | M.P., 98–99° C. |
| 102 | H₃C—C₆H₄—O(CH₂)₃—O—C₆H₄—NHC(=O)N(CH₃)₂ | M.P., 121–122° C. |
| 103 | 3,5-Cl₂C₆H₃—OCH₂CH₂OCH₂CH₂—O—C₆H₄—NHC(=O)N(OCH₃)(CH₃) | $n_D^{28}$ 1.5662 |
| 104 | 3,5-Cl₂C₆H₃—OCH₂CH₂OCH₂CH₂—O—C₆H₄—NHC(=O)N(CH₃)₂ | M.P., 91–92° C. |
| 105 | H₃C—C₆H₄—OCH₂CH₂OCH₂CH₂—O—C₆H₄—NHC(=O)N(OCH₃)(CH₃) | M.P., 74–76° C. |
| 106 | H₃C—C₆H₄—OCH₂CH₂OCH₂CH₂—O—C₆H₄—NHC(=O)N(CH₃)₂ | M.P., 55–56° C. |
| 107 | C₆H₅—O(CH₂)₈—O—C₆H₄—NHC(=O)N(OCH₃)(CH₃) | M.P., 60–61° C. |
| 108 | C₆H₅—O(CH₂)CH₈—O—C₆H₄—NHC(=O)N(CH₃)₂ | M.P., 125–126° C. |
| 109 | C₆H₅—CH₂OCH₂C(CH₃)₂—CH₂—S—C₆H₄—NHC(=O)N(OCH₃)(CH₃) | $n_D^{27.5}$ 1.5705 |
| 110 | C₆H₅—CH₂OCH₂C(CH₃)₂—CH₂—S—C₆H₄—NHC(=O)N(CH₃)₂ | M.P., 82–84° C. |

-continued

| Compound No. | Chemical structure | Melting point or refractive index |
| --- | --- | --- |
| 111 | H₃CS—⟨⟩—OCH₂CH₂OCH₂CH₂—S—⟨⟩—NHC(=O)N(OCH₃)(CH₃) | $n_D^{23.5}$ 1.5969 |
| 112 | H₃CS—⟨⟩—OCH₂CH₂OCH₂CH₂—S—⟨⟩—NHC(=O)N(CH₃)(CH₃) | $n_D^{22.5}$ 1.6041 |
| 113 | ⟨⟩—CH₂CH₂CH₂O—⟨⟩—NHC(=O)N(H)(CH₃) | M.P., 115–116° C. |
| 114 | ⟨⟩—SCH₂CH₂O—⟨⟩—NHC(=O)N(H)(CH₃) | M.P., 125–126° C. |
| 115 | ⟨⟩—CH₂CH₂CH₂O—⟨⟩(Cl)—NHC(=O)N(OCH₃)(CH₃) | $n_D^{24.0}$ 1.5404 |
| 116 | (2-CH₃)⟨⟩—(CH₂)₃—O—⟨⟩—NHC(=O)N(OCH₃)(CH₃) | M.P., 71–72° C. |
| 117 | (2-CH₃)⟨⟩—(CH₂)₃—O—⟨⟩—NHC(=O)N(CH₃)(CH₃) | M.P., 135–136° C. |
| 118 | (2-OCH₃)⟨⟩—(CH₂)₃—O—⟨⟩—NHC(=O)N(OCH₃)(CH₃) | M.P., 43–44.5° C. |
| 119 | (2-OCH₃)⟨⟩—(CH₂)₃—O—⟨⟩—NHC(=O)N(CH₃)(CH₃) | M.P., 129–130° C. |
| 120 | (3-CH₃)⟨⟩—(CH₂)₃—O—⟨⟩—NHC(=O)N(OCH₃)(CH₃) | M.P., 56–57° C. |

-continued

| Compound No. | Chemical structure | Melting point or refractive index |
|---|---|---|
| 121 | H₃C-C₆H₄-(CH₂)₃-O-C₆H₄-NHC(O)N(CH₃)CH₃ | M.P., 95–96° C. |
| 122 | H₃CO-C₆H₄-(CH₂)₃-O-C₆H₄-NHC(O)N(OCH₃)CH₃ | $n_D^{26.5}$ 1.5512 |
| 123 | H₃CO-C₆H₄-(CH₂)₃-O-C₆H₄-NHC(O)N(CH₃)CH₃ | M.P., 100–101° C. |
| 124 | H₃C-C₆H₄-(CH₂)₃-O-C₆H₄-NHC(O)N(OCH₃)CH₃ | M.P., 75–76° C. |
| 125 | H₃C-C₆H₄-(CH₂)₃-O-C₆H₄-NHC(O)N(CH₃)CH₃ | M.P., 110–111° C. |
| 126 | H₃CO-C₆H₄-(CH₂)₃-O-C₆H₄-NHC(O)N(OCH₃)CH₃ | M.P., 88–89° C. |
| 127 | H₃CO-C₆H₄-(CH₂)₃-O-C₆H₄-NHC(O)N(CH₃)CH₃ | M.P., 140–141° C. |
| 128 | C₆H₅-CH(CH₃)CH₂O-C₆H₄-NHC(O)N(OCH₃)CH₃ | $n_D^{26}$ 1.5409 |
| 129 | C₆H₅-CH(CH₃)CH₂O-C₆H₄-NHC(O)N(CH₃)CH₃ | $n_D^{26}$ 1.5420 |
| 130 | 2,4-(CH₃)₂C₆H₃-CH₂CH₂O-C₆H₄-NHC(O)N(OCH₃)CH₃ | M.P., 88–89° C. |

-continued

| Compound No. | Chemical structure | Melting point or refractive index |
|---|---|---|
| 131 | 2,5-dimethylphenyl-CH$_2$CH$_2$O-C$_6$H$_4$-NHC(O)N(CH$_3$)$_2$ | M.P., 138–139° C. |
| 132 | 2,4,6-trimethylphenyl-CH$_2$CH$_2$O-C$_6$H$_4$-NHC(O)N(OCH$_3$)(CH$_3$) | M.P., 74–75° C. |
| 133 | 2,4,6-trimethylphenyl-CH$_2$CH$_2$O-C$_6$H$_4$-NHC(O)N(CH$_3$)$_2$ | M.P., 189–190° C. |
| 134 | 2-Cl-C$_6$H$_4$-CH$_2$CH$_2$O-C$_6$H$_4$-NHC(O)N(OCH$_3$)(CH$_3$) | M.P., 58–59° C. |
| 135 | 2-Cl-C$_6$H$_4$-CH$_2$CH$_2$O-C$_6$H$_4$-NHC(O)N(CH$_3$)$_2$ | M.P., 94–95° C. |
| 136 | H$_5$C$_2$O-C$_6$H$_4$-CH$_2$CH$_2$O-C$_6$H$_4$-NHC(O)N(OCH$_3$)(CH$_3$) | $n_D^{27.5}$ 1.5640 |
| 137 | H$_5$C$_2$O-C$_6$H$_4$-CH$_2$CH$_2$O-C$_6$H$_4$-NHC(O)N(CH$_3$)$_2$ | M.P., 153–154° C. |
| 138 | F$_3$C-C$_6$H$_4$-CH$_2$CH$_2$O-C$_6$H$_4$-NHC(O)N(OCH$_3$)(CH$_3$) | M.P., 85–86° C. |
| 139 | F$_3$C-C$_6$H$_4$-CH$_2$CH$_2$O-C$_6$H$_4$-NHC(O)N(CH$_3$)$_2$ | M.P., 150–151° C. |
| 140 | Cl-C$_6$H$_4$-(CH$_2$)$_4$-O-C$_6$H$_4$-NHC(O)N(OCH$_3$)(CH$_3$) | M.P., 69–70° C. |

-continued

| Compound No. | Chemical structure | Melting point or refractive index |
|---|---|---|
| 141 | Cl—⟨⟩—(CH₂)₄—O—⟨⟩—NHC(=O)N(CH₃)(CH₃) | M.P., 123–124° C. |
| 142 | H₃C—⟨⟩—CH₂CH₂O—⟨⟩—NHC(=O)N(H)(CH₃) | M.P., 105–106° C. |
| 143 | Cl—⟨⟩—CH₂CH₂CH₂O—⟨⟩—NHC(=O)N(OCH₃)(CH₃) | M.P., 53–54 20 C. |
| 144 | Cl—⟨⟩—CH₂CH₂CH₂O—⟨⟩—NHC(=O)N(CH₃)(CH₃) | M.P., 119–120° C. |

In the practical application of the compounds (I), they may be applied as such or in any of the preparation forms such as wettable powders, emulsifiable concentrates, granules and dusts.

In producing such preparation forms, a solid or liquid carrier may be used. As the solid carrier, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As the liquid carrier, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion and spreading may be any of the nonionic, anionic, cationic and amphoteric type agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts, oxyalkylamines and the like. But the surface active agent is not of course limited to these compounds. And, if necessary, gelatin, casein, sodium alginate, starch, agar, polyvinyl alcohol or the like may be used as an auxiliary agent.

Examples of the herbicidal composition according to the present invention will be shown hereinafter. In these examples, part(s) are by weight.

EXAMPLE A

Eighty parts of the compound (I) (Compound No. 65), 5 parts of polyoxyethylene alkylaryl ether and 15 parts of synthetic silicon oxide hydrate are well mixed while being powdered. Thus, a dust is obtained.

EXAMPLE B

Thirty parts of the compound (I) (Compound No. 2 or 70), 7 parts of polyoxyethylene alkylaryl ether, 3 parts of alkylaryl sulfonate and 60 parts of xylene are well mixed. Thus, an emulsifiable concentrate is obtained.

EXAMPLE C

One part of the compound (I) (Compound No. 49), 1 part of white carbon, 5 parts of lignosulfonate and 93 parts of clay are well mixed while being powdered. The mixture is then well kneaded with water, granulated and dried to obtain a granule.

EXAMPLE D

Fourty parts of bentonite, 5 parts of lignosulfonate and 55 parts of clay are well mixed while being powdered. The mixture is well kneaded with water, granulated and dried to obtain a granule containing no active ingredient. Ninety-five parts of the granule is impregnated with 5 parts of the compound (I) (Compound No. 8, 44 or 55). Thus, a granule is obtained.

EXAMPLE H

Three parts of the compound (I) (Compound No. 57), 0.5 part of isopropyl phosphate, 66.5 parts of clay and 30 parts of talc are well mixed while being powdered. Thus, a dust is obtained.

EXAMPLE I

Twenty-five parts of the compound (I) (Compound No. 1 or 35), 2.5 parts of dodecylbenzenesulfonate, 2.5 parts of lignosulfonate and 70 parts of diatomaceous earth are well mixed while being powdered. Thus, a wettable powder is obtained.

The compounds (I) of the present invention may be used together with other herbicides to improve the herbicidal activity, and in some cases, a synergistic effect can be expected. As the other herbicides, there may be exemplified phenoxy series herbicides such as 2,4-dichlorophenoxybutyric acid (including esters and salts thereof); diphenyl ether series herbicides such as 2,4-dichlorophenyl-4'-nitrophenyl ether, 2,4,6-trichlorophenyl-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine and 2-methylthio-4,6-bisisopropylamino-1,3,5-triazine; triazine series herbicides such as 4-amino-6-tert-butyl-3-(methylthio)-1,2,4-triazine-5(4H)-one; urea series herbicides such as 3-(3,4-dichlorophenyl)-1,1-dimethylurea, 3-(3,4-dichlorophenyl)-1-methoxy-1-methylurea, 3-(3-chloro-4-difluorochloromethylthiophenyl)-1,1-dimethylurea, 3-[4-(4-chlorophenoxy)-phenyl]-1,1-dimethylurea and 3-($\alpha,\alpha,\alpha$-trifluoro-m-tolyl)-1,1-dimethylurea; carbamate series herbicides such as isopropyl N-(3-chlorophenyl)carbamate, methyl N-(3,4-dichlorophenyl)carbamate and 4-chloro-2-butynyl-m-chlorocarbanilate; thiocarbamate series herbicides such as S-(4-chlorobenzyl)-N,N-diethylthiolcarbamate, S-ethyl N,N-hexamethylenethiolcarbamate and S-ethyl dipropylthiolcarbamate; acid anilide series herbicides such as 3,4-dichloropropionanilide, N-methoxymethyl-2,6-diethyl-2-chloroacetanilide and 2-chloro-2',6'-diethyl-N-(butoxymethyl)acetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N-(phosphonomethyl)glycine, O-ethyl O-(2-nitro-5-methylphenyl)-N-sec-butylphosphoroamidothioate and O-methyl O-(2-nitro-4-methylphenyl)-N-isopropylphosphoroamidothioate; toluidine series herbicides such as $\alpha,\alpha,\alpha$-trifluoro-2,6-dinitro-N,N-dipropyl-p-toluidine and N-(cyclopropylmethyl)-$\alpha,\alpha,\alpha$-trifluoro-2,6-dinitro-N-propyl-p-toluidine; N-sec-butyl-4-tert-butyl-2,6-dinitroaniline; 3,5-dinitro-$N^4,N^4$-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazine-(4)-3H-one-2,2-dioxide (including salts thereof); $\alpha$-($\beta$-naphthoxy)propionanilide; 2-($\alpha$-naphthoxy)-N,N-diethylpropionamide; 3-amino-2,5-dichlorobenzoic acid; 2-sec-butyl-4,6-dinitrophenol; N-1-naphthylphthalamic acid; 2-(1-allyloxyamino)butylidene-5,5-dimethyl-4-methoxycarbonylcyclohexane-1,3-dione (including salts thereof) and the like. But, the herbicides are not of course limited to these examples.

The herbicides of the present invention may be applied together with fungicides, microbial insecticides, organo-phosphorus series insecticides, carbamate series insecticides, pyrethroid series insecticides, plant growth regulators, fertilizers, etc.

The present invention will be illustrated in more detail with reference to the following Examples.

EXAMPLE 1 (METHOD (A))

To a solution of 3-[2-(3-methoxyphenyl)ethoxy]-phenyl isocyanate (5.2 g) in benzene (100 ml), a solution of N,O-dimethylhydroxylamine (2 g) in benzene (50 ml) was added dropwise at a temperature below 30° C. The reaction mixture was allowed to stand at room temperature for 30 minutes, and the solvent was removed under reduced pressure. The residue was recrystallized from ethanol to obtain 4.3 g of N'-3-[2-(3-methoxyphenyl)ethoxy]phenyl-N-methoxy-N-methylurea (Compound No. 11) as white needles. M.P., 53°–54° C.

Elementary analysis: Calcd. for $C_{18}H_{22}O_4H_2$ (%): C, 65.44; H, 6.71; N, 8.48. Found (%): C, 65.23; H, 6.83; N, 8.52.

NMR $_{CDCl_3}{}^\delta$: 3.02 (t, 2H); 3.15 (s, 3H); 3.72 (s, 3H); 3.78 (s, 3H); 4.17 (t, 2H); 6.40–7.35 (8H); 7.60 (s, 1H).

In the same manner as above, the compounds (I) such as Compound Nos. 7, 13, 15, 17, 19, 21, 23, 27 and 30 were synthesized.

EXAMPLE 2 (METHOD (A))

To a solution of 3-phenethyloxyphenyl isocyanate (15 g) in benzene (200 ml), a solution of dimethylamine (6 g) in benzene (100 ml) was added dropwise at a temperature below 30° C. The reaction mixture was allowed to stand at room temperature for 1 hour, and the solvent was removed under reduced pressure. The residue was recrystallized from ethanol to obtain 13.6 g of N'-3-phenethyloxyphenyl-N,N-dimethylurea (Compound No. 2) as white needles. M.P., 100°–101° C.

Elementary analysis: Calcd. for $C_{17}H_{20}O_2N_2$ (%): C, 71.80; H, 7.09; N, 9.85. Found (%): C, 71.84; H, 7.06; N, 9.84.

NMR $_{CDCl_3}{}^\delta$: 2.94 (s, 6H); 3.02 (t, 2H); 4.10 (t, 2H); 6.20–7.40 (10H).

In the same manner as above, the compounds (I) such as Compound Nos. 4, 6, 8, 10, 12, 18, 22, 24 and 31 were synthesized.

EXAMPLE 3 (METHOD (A))

To a solution of 3-[2-(4-chlorophenyl)ethoxy]-phenyl isocyanate (10 g) in benzene (150 ml), a solution of monomethylamine in benzene (100 ml) was added dropwise at a temperature below 30° C. The reaction mixture was allowed to stand at room temperature for 1 hour, and the solvent was removed under reduced pressure. The residue was recrystallized from ethanol to obtain 7.3 g of N'-3-[2-(4-chlorophenyl)ethoxy]phenyl-N-methylurea (Compound No. 33) as white needles. M.P., 126°–127° C.

Elementary analysis: Calcd. for $C_{16}H_{17}O_2N_2Cl$ (%): C, 63.05; H, 5.62; N, 9.19; Cl, 11.63. Found (%): C, 63.09; H, 5.58; N, 9.16; Cl, 11.67.

NMR $_{CDCl_3\text{-}DMSO}{}^\delta$: 2.69 (d, 3H); 3.00 (t, 2H); 4.06 (t, 2H); 5.80 (m, 1H); 6.20–7.30 (8H); 8.17 (s, 1H).

In the same manner as above, the compounds (I) such as Compound No. 32 were synthesized.

EXAMPLE 4 (METHOD (B))

A solution of 3-phenethyloxyphenyl isocyanate (4.8 g) in methylene chloride (60 ml) was added dropwise to a solution of hydroxylamine hydrochloride (5 g) and sodium hydroxide (2.8 g) in water (10 ml) at a temperature below 20° C. The precipitated crystals were collected by filtration and dried to obtain 4 g of N'-3-phenethyloxyphenyl-N-hydroxyurea. To a solution of the hydroxyurea derivative (4 g) in a benzene/methanol (1:1) mixture (150 ml) were alternatively added dimethyl sulfate (2.8 ml) and an aqueous solution of sodium hydroxide (10 N, 6 ml) at a temperature below 30° C. After stirring at room temperature, the reaction solution was diluted with water and extracted with benzene. The solvent was removed from the extract under reduced pressure, and the residue was recrystallized from ethanol to obtain 1.8 g of N'-3-phenethyloxyphenyl-N-methoxy-N-methylurea (Compound No. 1) as white prisms. M.P., 82.0°–82.5° C.

Elementary analysis: Calcd. for $C_{17}H_{20}N_2O_3$ (%): C, 67.98; H, 6.71; N, 9.33. Found (%): C, 67.83; H, 6.82; N, 9.31.

NMR $_{CDCl_3}{}^\delta$: 3.04 (t, 2H); 3.12 (s, 3H); 3.69 (s, 3H); 4.14 (t, 2H); 6.40–7.40 (9H); 7.60 (s, 1H).

In the same manner as above, the compounds (I) such as Compound Nos. 9 and 25 were synthesized.

EXAMPLE 5 (METHOD (D))

To a solution of sodium ethoxide (2 g) in N,N-dimethylformamide (100 ml), N'-3-hydroxyphenyl-N-methoxy-N-methylurea (4 g) was added. Thereafter, a solution of 2-(2-methylphenyl)ethyl bromide (4 g) in N,N-dimethylformamide (50 ml) was dropwise added thereto. The reaction mixture was slowly heated, kept at 90° to 100° C. for 3 hours, poured into ice water and extracted with benzene. The solvent was removed under reduced pressure, and the residue was recrystallized from ethanol to obtain 3.2 g of N'-3-[2-(2-methylphenyl)ethoxy]phenyl-N-methoxy-N-methylurea (Compound No. 3) as white needles. M.P., 88°–89° C.

Elementary analysis: Calcd. for $C_{18}H_{22}O_3N_2$ (%): C, 68.77; H, 7.05; N, 8.91. Found (%): C, 68.46; H, 7.03; N, 8.92.

NMR $_{CDCl_3}{}^\delta$: 2.35 (s, 3H); 3.09 (t, 2H); 3.15 (s, 3H); 3.70 (s, 3H); 4.13 (t, 2H); 6.40–7.30 (8H); 7.55 (s, 1H).

In the same manner as above, the compounds (I) such as Compound Nos. 5, 14, 16, 20, 26, 28 and 29 were synthesized.

EXAMPLE 6 (METHOD (A))

To a solution of 3-phenethylthiophenyl isocyanate (25.5 g) in benzene (300 ml) was added dropwise a solution of N,O-dimethylhydroxylamine (8 g) in benzene (100 ml) at 20° to 30° C. After stirring at room temperature for a while, the solvent was removed under reduced pressure. The residue was recrystallized from ethanol to obtain 30.5 g of N'-3-phenethylthiophenyl-N-methoxy-N-methylurea (Compound No. 34) as white needles. M.P., 76°–77° C.

Elementary analysis: Calcd. for $C_{17}H_{20}O_2N_2S$ (%): C, 64.53; H, 6.37; N, 8.86; S, 10.13. Found (%): C, 64.30; H, 6.44; N, 8.69; S, 9.90.

NMR $_{CDCl_3}{}^\delta$: 3.01 (m, 4H); 3.10 (s, 3H); 3.68 (s, 3H); 6.80–7.50 (9H); 7.59 (s, 1H).

In the same manner as above, the compounds (I) such as Compound Nos. 35, 36, 41, 43, 44 and 46 were synthesized.

EXAMPLE 7 (METHOD (B))

A solution of 3-(4-chlorophenethylthio)phenyl isocyanate (15 g) in methylene chloride (50 ml) was added dropwise to a solution of hydroxylamine hydrochloride (7 g) and sodium hydroxide (4 g) in water (15 ml) at a temperature below 20° C. After dilution with water, the precipitated crystals were collected by filtration and dried to obtain 16.3 g of N'-3-(4-chlorophenethylthio)-phenyl-N-hydroxyurea. Thereafter, 16.3 g of the hydroxyurea derivative were dissolved in a benzene/methanol (1:1) mixture, and 10 ml of 10 N aqueous sodium hydroxide solution and 12 g of dimethyl sulfate were added dropwise thereto at a temperature below 30° C. After stirring at room temperature, the reaction mixture was diluted with water and extracted with benzene. The solvent was removed from the extract under reduced pressure, and the residue was recrystallized from ethanol to obtain 13.4 g of N'-3-(4-chlorophenethylthio)phenyl-N-methoxy-N-methylurea (Compound No. 45) as white needles.

M.P., 88°–89° C.

Elementary analysis: Calcd. for $C_{17}H_{19}O_2N_2ClS$ (%): C, 58.19; H, 5.46; N, 8.00; Cl, 10.11; S, 9.14. Found (%): C, 57.99; H, 5.55; N, 7.89; Cl, 10.13; S, 9.01.

NMR $_{CDCl_3}{}^\delta$: 2.97 (m, 4H); 3.11 (s, 3H); 3.68 (s, 3H); 6.70–7.55 (8H); 7.65 (s, 1H).

In the same manner as above, the compounds (I) such as Compound Nos. 37 and 39 were synthesized.

EXAMPLE 8 (METHOD (D))

To a solution of sodium ethoxide (6.8 g) in N,N-dimethylformamide (200 ml) was added N'-3-mercaptophenyl-N,N-dimethylurea (20 g), and a solution of 2-methylphenethyl bromide (20 g) in N,N-dimethylformamide (100 ml) was dropwise added thereto. The reaction mixture was gradually heated, kept at 100° C. for 5 hours and poured into ice water, followed by extraction with benzene. The solvent was removed from the extract under reduced pressure, and the residue was recrystallized from ethanol to obtain 24.5 g of N'-3-(2-methylphenethylthio)phenyl-N,N-dimethylurea (Compound No. 38) as white needles. M.P., 128°–129° C.

Elementary analysis: Calcd. for $C_{18}H_{22}OH_2S$ (%): C, 68.75; H, 7.05; N, 8.91; S, 10.20. Found (%): C, 68.49; H, 7.26; N, 8.63; S, 9.99.

NMR $_{CDCl_3}{}^\delta$: 2.22 (s, 3H); 2.91 (m, 4H); 2.93 (s, 6H); 6.41 (s, 1H); 6.60–7.40 (8H).

In the same manner as above, the compounds (I) such as Compound Nos. 40, 42, 47 and 48 were synthesized.

EXAMPLE 9 (METHOD (A))

To a solution of 3-(3-phenylpropoxy)phenyl isocyanate (12.7 g) in benzene (100 ml) was added dropwise a solution of N,O-dimethylhydroxylamine (5 g) in benzene (50 ml) at 20° to 30° C. The reaction mixture was stirred at the same temperature for an additional 30 minutes. The solvent was removed under reduced pressure, and the residue was recrystallized from ethanol to obtain 11.5 g of N'-3-(3-phenylpropoxy)phenyl-N-methoxy-N-methylurea (Compound No. 49) as white needles. M.P., 82°–83° C.

Elementary analysis: Calcd. for $C_{18}H_{22}N_2O_3$ (%): C, 68.77; H, 7.05; N. 8.91. Found (%): C, 68.79; H, 7.06; N, 8.88.

NMR $_{CDCl_3}{}^\delta$: 2.05 (m, 2H); 2.75 (t, 2H); 3.09 (s, 3H), 3.61 (s, 3H); 3.88 (t, 2H); 6.85–7.30 (9H); 7.61 (s, 1H).

In the same manner as above, the compounds (I) such as Compound Nos. 50, 51, 52, 53, 56, 58, 63, 64, 70, 71, 74, 75, 76, 77, 78, 79, 80, 93, 94, 101, 102, 109, 110, 111, 112, 113, 114, 115, 118, 119, 120, 121, 122, 123, 124, 125, 126, 127, 128, 129, 134, 135, 138, 139, 140, 141, 143 and 144 were synthesized.

EXAMPLE 10 (METHOD (B))

A solution of 3-[3-(3,4-dichlorophenyl)propoxy]-phenyl isocyanate (16.1 g) in methylene chloride (50 ml) was added dropwise to a solution of hydroxylamine hydrochloride (3.5 g) and sodium hydroxide (2.1 g) in water (15 ml) at a temperature below 20° C. After dilution with water, the precipitated crystals were collected by filtration and dried to obtain 15.3 g of N'-3-[3-(3,4-dichlorophenyl)propoxy]-phenyl-N-hydroxyurea. To a solution of the hydroxyurea derivative (15.3 g), dimethyl sulfate (22 g) and tetra-n-butylammonium bromide (0.15 g) in toluene (240 ml) was added dropwise an aqueous solution of sodium hydroxide (10 N, 17.0 ml). The reaction mixture was stirred at room temperature, diluted with water and extracted with benzene. After washing the benzene layer with water, the solvent was removed under reduced pressure. The residue was recrystallized from ethanol to obtain 13.6 g of N'-3-[3-(3,4-dichlorophenyl)-propoxy]phenyl-N-methoxy-N-methylurea (Compound No. 55) as white needles. M.P., 68°–69° C.

Elementary analysis: Calcd. for $C_{18}H_{20}Cl_2N_2O_3$ (%): C, 56.40; H, 5.26; N, 7.31; Cl, 18.50. Found (%): C, 56.46; H, 5.25; N, 7.30; Cl, 18.50.

NMR $_{CDCl_3}\delta$: 2.01 (m, 2H); 2.72 (t, 2H); 3.11 (s, 3H); 3.66 (s, 3H); 3.89 (t, 2H); 6.30–7.30 (7H); 7.55 (s, 1H).

In the same manner as above, the compounds (I) such as Compound Nos. 59, 65, 69, 81, 83, 87, 89, 91, 95, 99, 107, 116, 130 and 136 were synthesized.

EXAMPLE 11 (METHOD) (C))

A solution of 3-(4-phenylbutoxy)aniline (25 g), 40 % aqueous sodium hydroxide solution (100 ml) and N,N-dimethylcarbamyl chloride (17 g) in toluene (200 ml) was heated under reflux for 10 hours. The reaction mixture was allowed to stand at room temperature. The toluene layer was washed with water, and the solvent was removed under reduced pressure. The residue was recrystallized from ethanol to obtain 20.6 g of N'-3-(4-phenylbutoxy)phenyl-N,N-dimethylurea (Compound No. 66) as white needles. M.P., 115°–116° C.

Elementary analysis: Calcd. for $C_{19}H_{24}N_2O_2$ (%): C, 73.04; H, 7.74; N, 8.97. Found (%): C, 72.89; H, 7.88; N, 8.80.

NMR $_{CDCl_3}\delta$: 1.72 (m, 4H); 2.62 (t, 2H); 2.90 (s, 6H); 3.86 (t, 2H); 6.40–7.30 (10H).

In the same manner as above, the compounds (I) such as Compound Nos. 54, 60, 82, 88, 92, 100, 108, 117, 131, 137 and 142 were synthesized.

EXAMPLE 12 (METHOD (D))

To a solution of sodium ethoxide (6.8 g) in N,N-dimethylformamide (200 ml) was added 20 g of N'-(3-hydroxyphenyl)-N-methoxy-N-methylurea, and a solution of 3-(4-methylphenyl)propyl bromide (21 g) in N,N-dimethylformamide (100 ml) was added dropwise thereto. The reaction mixture was gradually heated, kept at 100° C. for 5 hours and poured into ice water. Precipitated crystals were collected by filtration, washed with water, ethanol and ether in order, air-dried and recrystallized from ethanol to obtain 27 g of N'-3-[3-(4-methylphenyl)propoxy]phenyl-N-methoxy-N-methylurea (Compound No. 57) as white needles. M.P., 75°–76° C.

Elementary analysis: Calcd. for $C_{19}H_{24}N_2O_3$ (%): C, 69.49; H, 7.37; N, 8.53. Found (%): 69.23; H, 7.53; N, 8.49.

NMR $_{CDCl_3}\delta$: 2.01 (m, 2H); 2.30 (s, 3H); 2.25 (t, 2H); 3.11 (s, 3H); 3.67 (s, 3H); 3.90 (t, 2H); 6.40–7.30 (8H); 7.62 (s, 1H).

In the same manner as above, the compounds (I) such as Compound Nos. 61, 62, 67, 68, 72, 73, 84, 85, 86, 90, 96, 97, 98, 103, 104, 105, 106, 132 and 133 were synthesized.

The application of the compounds (I) as herbicides will be illustrated in the following Examples wherein the phytotoxicity to crop plants and the herbicidal activity against weeds were evaluated as follows:

The aerial parts of treated test plants were cut off and weighed (fresh weight); the percentage of the fresh weight of the treated plot to that of the untreated plot was calculated. The phytotoxicity to cultivated plants and the herbicidal activity against weeds were expressed in an integer ranging from 0 to 5 according to the criteria shown in the following table. The rating values, 5 and 4, are generally regarded as acceptable in the efficacy to protect the cultivated plants from the weeds. The rating values in the paddy rice test alone were calculated from the dry weight of the plants.

| Rating value | Fresh weight (percentage to untreated plot) | |
|---|---|---|
| | Crop plant | Weeds |
| 5 | 100 | 0 |
| 4 | 99–90 | 1–10 |
| 3 | 89–80 | 11–20 |
| 2 | 79–60 | 21–40 |
| 1 | 59–40 | 41–60 |
| 0 | 39–0 | 61–100 |

The following control compounds were used in the examples.

Control compound (a):

[Structure: phenyl-CH₂O-phenyl-NHC(O)N(CH₃)CH₃]

MCP:

[Structure: Cl-phenyl(CH₃)-OCH₂COOH]

Diuron:

[Structure: Cl,Cl-phenyl-NHC(O)N(CH₃)CH₃]

Atrazine:

[Structure: triazine ring with i-H₇C₃HN, Cl, NHC₂H₅ substituents]

Barban:

[Structure: Cl-phenyl-NHCOCH₂C≡CCH₂Cl]

Fluometuron: 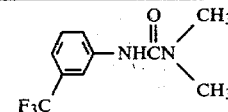

Chloroxuron: 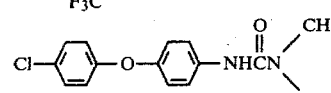

Bentazon: 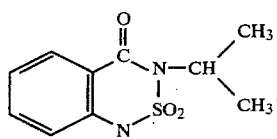

Chloramben: 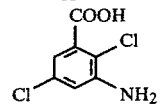

EXAMPLE 13 (PADDY RICE TEST)

Wagner's pots (1/5000 are) were each filled with 1.5 kg of paddy field soil containing seeds of weeds and kept under flooded conditions. Seedlings of rice plants at the third-leaf stage were transplanted thereto and grown for 5 days. Thereafter, a required amount of the wettable powder of each test compound was diluted with water and applied to the soil under flooded conditions. Twenty-five days after the application, the evaluation of the herbicidal activity and the phytotoxicity was made against rice plants, barnyard grass, broad-leaved weeds (e.g. pickerel weed, false pimpernel, tooth cup) and nutsedge sp.

The results are shown in Table 1.

TABLE 1

| Compound No. | Dosage (weight of active, ingredient, g/are) | Phytotoxicity Rice plant | Herbicidal activity | | |
|---|---|---|---|---|---|
| | | | Barnyard grass | Broad-leaved weeds | Nut-sedge |
| 1 | 20 | 5 | 5 | 5 | 5 |
| | 10 | 5 | 4 | 5 | 5 |
| | 5 | 5 | 3 | 5 | 5 |
| 2 | 20 | 5 | 4 | 5 | 5 |
| | 10 | 5 | 4 | 5 | 5 |
| | 5 | 5 | 3 | 5 | 5 |
| 3 | 20 | 4 | 5 | 5 | 5 |
| | 10 | 5 | 4 | 5 | 5 |
| | 5 | 5 | 4 | 5 | 5 |
| 4 | 20 | 5 | 5 | 5 | 5 |
| | 10 | 5 | 4 | 5 | 5 |
| | 5 | 5 | 3 | 5 | 5 |
| 5 | 20 | 5 | 5 | 5 | 5 |
| | 10 | 5 | 4 | 5 | 5 |
| | 5 | 5 | 3 | 5 | 5 |
| 6 | 20 | 4 | 5 | 5 | 5 |
| | 10 | 5 | 4 | 5 | 5 |
| | 5 | 5 | 4 | 5 | 5 |
| 7 | 20 | 5 | 4 | 5 | 5 |
| | 10 | 5 | 4 | 5 | 5 |
| | 5 | 5 | 2 | 5 | 4 |
| 8 | 20 | 5 | 5 | 5 | 5 |
| | 10 | 5 | 4 | 5 | 5 |
| | 5 | 5 | 3 | 5 | 5 |
| 9 | 20 | 5 | 5 | 5 | 5 |
| | 10 | 5 | 4 | 5 | 5 |
| | 5 | 5 | 3 | 5 | 5 |
| 10 | 20 | 5 | 5 | 5 | 5 |
| | 10 | 5 | 4 | 5 | 5 |
| | 5 | 5 | 3 | 5 | 5 |
| 11 | 20 | 4 | 5 | 5 | 5 |
| | 10 | 5 | 5 | 5 | 5 |
| | 5 | 5 | 4 | 5 | 5 |
| 12 | 20 | 5 | 5 | 5 | 5 |
| | 10 | 5 | 4 | 5 | 5 |
| | 5 | 5 | 3 | 5 | 5 |
| 13 | 20 | 5 | 5 | 5 | 5 |
| | 10 | 5 | 4 | 5 | 5 |
| | 5 | 5 | 4 | 5 | 5 |
| 14 | 20 | 5 | 5 | 5 | 5 |
| | 10 | 5 | 5 | 5 | 5 |
| | 5 | 5 | 4 | 5 | 5 |
| 15 | 20 | 5 | 5 | 5 | 5 |
| | 10 | 5 | 4 | 5 | 5 |
| | 5 | 5 | 3 | 5 | 5 |
| 16 | 20 | 5 | 4 | 5 | 5 |
| | 10 | 5 | 4 | 5 | 5 |
| | 10 | 5 | 4 | 5 | 5 |
| | 5 | 5 | 3 | 5 | 4 |
| 17 | 20 | 5 | 4 | 5 | 5 |
| | 10 | 5 | 3 | 5 | 4 |
| | 5 | 5 | 3 | 5 | 4 |
| 18 | 40 | 5 | 4 | 5 | 5 |
| | 20 | 5 | 4 | 5 | 4 |
| | 10 | 5 | 3 | 5 | 4 |
| 19 | 20 | 5 | 5 | 5 | 5 |
| | 10 | 5 | 4 | 5 | 5 |
| | 5 | 5 | 4 | 5 | 5 |
| 20 | 20 | 5 | 4 | 5 | 5 |
| | 10 | 5 | 4 | 5 | 5 |
| | 5 | 5 | 3 | 5 | 5 |
| 21 | 20 | 5 | 5 | 5 | 5 |
| | 10 | 5 | 4 | 5 | 5 |
| | 5 | 5 | 3 | 5 | 5 |
| 22 | 20 | 5 | 4 | 5 | 5 |
| | 10 | 5 | 3 | 5 | 4 |
| 23 | 20 | 5 | 4 | 5 | 5 |
| | 10 | 5 | 3 | 5 | 5 |
| | 5 | 5 | 3 | 5 | 5 |
| 24 | 20 | 5 | 4 | 5 | 5 |
| | 10 | 5 | 4 | 5 | 4 |
| | 5 | 5 | 3 | 5 | 3 |
| 25 | 20 | 5 | 4 | 5 | 5 |
| | 10 | 5 | 4 | 5 | 5 |
| | 5 | 5 | 3 | 5 | 4 |
| 26 | 40 | 5 | 4 | 5 | 5 |
| | 20 | 5 | 4 | 5 | 4 |
| | 10 | 5 | 3 | 5 | 4 |
| 27 | 20 | 5 | 5 | 5 | 5 |
| | 10 | 5 | 4 | 5 | 5 |
| | 5 | 5 | 3 | 5 | 5 |
| 28 | 20 | 5 | 5 | 5 | 5 |
| | 10 | 5 | 4 | 5 | 5 |
| | 5 | 5 | 3 | 5 | 5 |
| 29 | 20 | 5 | 4 | 5 | 5 |
| | 10 | 5 | 4 | 5 | 5 |
| | 5 | 5 | 3 | 5 | 4 |
| 30 | 20 | 5 | 5 | 5 | 5 |
| | 10 | 5 | 4 | 5 | 5 |
| | 5 | 5 | 3 | 5 | 5 |
| 31 | 20 | 5 | 5 | 5 | 5 |
| | 10 | 5 | 4 | 5 | 5 |
| | 5 | 5 | 3 | 5 | 5 |
| 32 | 20 | 5 | 4 | 5 | 5 |
| | 10 | 5 | 4 | 5 | 5 |
| | 5 | 5 | 3 | 5 | 5 |
| 33 | 20 | 5 | 4 | 5 | 5 |
| | 10 | 5 | 4 | 5 | 5 |
| | 5 | 5 | 3 | 5 | 5 |
| 34 | 20 | 5 | 5 | 5 | 5 |
| | 10 | 5 | 4 | 5 | 5 |
| 35 | 20 | 5 | 4 | 5 | 5 |
| | 10 | 5 | 4 | 5 | 5 |
| 36 | 20 | 5 | 4 | 5 | 5 |
| | 10 | 5 | 4 | 5 | 5 |
| 37 | 20 | 5 | 5 | 5 | 5 |
| | 10 | 5 | 4 | 5 | 5 |

TABLE 1-continued

| Compound No. | Dosage (weight of active, ingredient, g/are) | Phytotoxicity Rice plant | Herbicidal activity | | |
|---|---|---|---|---|---|
| | | | Barnyard grass | Broad-leaved weeds | Nutsedge |
| 38 | 20 | 5 | 4 | 5 | 5 |
| | 10 | 5 | 4 | 5 | 5 |
| 39 | 20 | 5 | 5 | 5 | 5 |
| | 10 | 5 | 5 | 5 | 5 |
| 40 | 20 | 5 | 5 | 5 | 5 |
| | 10 | 5 | 4 | 5 | 5 |
| 41 | 20 | 5 | 5 | 5 | 5 |
| | 10 | 5 | 4 | 5 | 5 |
| 42 | 20 | 5 | 4 | 5 | 5 |
| | 10 | 5 | 4 | 5 | 5 |
| 43 | 20 | 5 | 5 | 5 | 5 |
| | 10 | 5 | 5 | 5 | 5 |
| 44 | 20 | 5 | 5 | 5 | 5 |
| | 10 | 5 | 4 | 5 | 5 |
| 45 | 20 | 5 | 5 | 5 | 5 |
| | 10 | 5 | 5 | 5 | 5 |
| 46 | 20 | 5 | 5 | 5 | 5 |
| | 10 | 5 | 5 | 5 | 5 |
| 47 | 20 | 5 | 5 | 5 | 5 |
| | 10 | 5 | 5 | 5 | 5 |
| 48 | 20 | 5 | 5 | 5 | 5 |
| | 10 | 5 | 4 | 5 | 5 |
| 49 | 20 | 5 | 5 | 5 | 5 |
| | 10 | 5 | 5 | 5 | 5 |
| 50 | 20 | 5 | 5 | 5 | 5 |
| | 10 | 5 | 5 | 5 | 5 |
| 51 | 20 | 4 | 5 | 5 | 5 |
| | 10 | 5 | 5 | 5 | 5 |
| 52 | 20 | 4 | 5 | 5 | 5 |
| | 10 | 5 | 5 | 5 | 5 |
| 53 | 20 | 5 | 5 | 5 | 5 |
| | 10 | 5 | 5 | 5 | 5 |
| 54 | 20 | 5 | 5 | 5 | 5 |
| | 10 | 5 | 4 | 5 | 5 |
| 55 | 20 | 5 | 5 | 5 | 5 |
| | 10 | 5 | 5 | 5 | 5 |
| 56 | 20 | 5 | 5 | 5 | 5 |
| | 10 | 5 | 4 | 5 | 5 |
| 57 | 20 | 4 | 5 | 5 | 5 |
| | 10 | 5 | 5 | 5 | 5 |
| 58 | 20 | 5 | 5 | 5 | 5 |
| | 10 | 5 | 5 | 5 | 5 |
| 59 | 20 | 5 | 5 | 5 | 5 |
| | 10 | 5 | 5 | 5 | 5 |
| 60 | 20 | 5 | 5 | 5 | 5 |
| | 10 | 5 | 5 | 5 | 5 |
| 61 | 20 | 4 | 5 | 5 | 5 |
| | 10 | 5 | 5 | 5 | 5 |
| 62 | 20 | 4 | 5 | 5 | 5 |
| | 10 | 5 | 5 | 5 | 5 |
| 65 | 20 | 5 | 5 | 5 | 5 |
| | 10 | 5 | 5 | 5 | 5 |
| 66 | 20 | 5 | 4 | 5 | 5 |
| | 10 | 5 | 4 | 5 | 5 |
| 68 | 20 | 5 | 4 | 5 | 5 |
| | 10 | 5 | 4 | 5 | 5 |
| 69 | 20 | 5 | 5 | 5 | 5 |
| | 10 | 5 | 5 | | 5 |
| 70 | 20 | 5 | 5 | 5 | 5 |
| | 10 | 5 | 5 | 5 | 5 |
| 71 | 40 | 5 | 4 | 5 | 5 |
| | 20 | 5 | 4 | 5 | 5 |
| 72 | 40 | 5 | 4 | 5 | 5 |
| | 20 | 5 | 4 | 5 | 4 |
| 73 | 20 | 4 | 5 | 5 | 5 |
| | 10 | 5 | 5 | 5 | 5 |
| 74 | 20 | 5 | 4 | 5 | 5 |
| | 10 | 5 | 4 | 5 | 5 |
| 75 | 20 | 5 | 5 | 5 | 5 |
| | 10 | 5 | 5 | 5 | 5 |
| 80 | 20 | 5 | 4 | 5 | 5 |
| | 10 | 5 | 4 | 5 | 5 |
| 81 | 20 | 5 | 5 | 5 | 5 |
| | 10 | 5 | 5 | 5 | 5 |
| 82 | 20 | 5 | 5 | 5 | 5 |
| | 10 | 5 | 4 | 5 | 5 |
| 83 | 20 | 5 | 5 | 5 | 5 |
| | 10 | 5 | 5 | 5 | 5 |
| 84 | 20 | 5 | 5 | 5 | 5 |
| | 10 | 5 | 4 | 5 | 5 |
| 85 | 20 | 5 | 4 | 5 | 5 |
| | 10 | 5 | 4 | 5 | 5 |
| 87 | 20 | 4 | 5 | 5 | 5 |
| | 10 | 5 | 5 | 5 | 5 |
| 88 | 40 | 5 | 4 | 5 | 5 |
| | 20 | 5 | 5 | 4 | |
| 89 | 20 | 5 | 5 | 5 | 5 |
| | 10 | 5 | 5 | 5 | 5 |
| 90 | 20 | 5 | 4 | 5 | 5 |
| | 10 | 5 | 3 | 5 | 4 |
| 92 | 20 | 5 | 4 | 5 | 5 |
| | 10 | 5 | 4 | 5 | 5 |
| 94 | 20 | 5 | 5 | 5 | 5 |
| | 10 | 5 | 5 | 5 | 5 |
| 95 | 20 | 5 | 4 | 5 | 5 |
| | 10 | 5 | 4 | 5 | 5 |
| 96 | 20 | 5 | 4 | 5 | 5 |
| | 10 | 5 | 4 | 5 | 5 |
| 99 | 20 | 5 | 5 | 5 | 5 |
| | 10 | 5 | 5 | 5 | 5 |
| 100 | 20 | 5 | 4 | 5 | 5 |
| | 10 | 5 | 3 | 5 | 4 |
| 101 | 20 | 5 | 5 | 5 | 5 |
| | 10 | 5 | 5 | 5 | 5 |
| 104 | 20 | 5 | 4 | 5 | 5 |
| | 10 | 5 | 4 | 5 | 4 |
| 106 | 20 | 5 | 5 | 5 | 5 |
| | 10 | 5 | 4 | 5 | 5 |
| 108 | 40 | 5 | 4 | 5 | 5 |
| | 20 | 5 | 4 | 5 | 4 |
| 109 | 40 | 5 | 4 | 5 | 5 |
| | 20 | 5 | 3 | 5 | 4 |
| 111 | 40 | 5 | 4 | 5 | 5 |
| | 20 | 5 | 4 | 5 | 5 |
| 113 | 40 | 5 | 4 | 5 | 5 |
| | 20 | 5 | 3 | 5 | 5 |
| 114 | 40 | 5 | 4 | 5 | 5 |
| | 20 | 5 | 3 | 5 | 4 |
| 115 | 40 | 5 | 4 | 5 | 5 |
| | 20 | 5 | 4 | 5 | 5 |
| 116 | 20 | 5 | 4 | 5 | 5 |
| | 10 | 5 | 4 | 5 | 5 |
| 117 | 40 | 5 | 4 | 5 | 5 |
| | 20 | 5 | 3 | 5 | 5 |
| 118 | 20 | 5 | 4 | 5 | 5 |
| | 10 | 5 | 4 | 5 | 5 |
| 119 | 20 | 5 | 4 | 5 | 5 |
| | 10 | 5 | 3 | 5 | 5 |
| 120 | 20 | 5 | 5 | 5 | 5 |
| | 10 | 5 | 4 | 5 | 5 |
| 121 | 20 | 5 | 4 | 5 | 5 |
| | 10 | 5 | 4 | 5 | 5 |
| 122 | 20 | 5 | 4 | 5 | 5 |
| | 10 | 5 | 3 | 5 | 5 |
| 124 | 20 | 5 | 5 | 5 | 5 |
| | 10 | 5 | 5 | 5 | 5 |
| 125 | 20 | 5 | 4 | 5 | 5 |
| | 10 | 5 | 3 | 5 | 5 |
| 126 | 20 | 5 | 4 | 5 | 5 |
| | 10 | 5 | 3 | 5 | 5 |
| 127 | 40 | 5 | 4 | 5 | 5 |
| | 20 | 5 | 3 | 5 | 5 |
| 130 | 40 | 5 | 4 | 5 | 5 |
| | 20 | 5 | 3 | 4 | 5 |
| 131 | 20 | 5 | 4 | 5 | 5 |
| | 10 | 5 | 3 | 5 | 5 |
| 132 | 20 | 5 | 4 | 5 | 5 |
| | 10 | 5 | 4 | 5 | 5 |
| 134 | 20 | 4 | 5 | 5 | 5 |
| | 10 | 5 | 4 | 5 | 5 |
| 135 | 20 | 5 | 4 | 5 | 5 |
| | 10 | 5 | 4 | 5 | 5 |

TABLE 1-continued

| Compound No. | Dosage (weight of active, ingredient, g/are) | Phytotoxicity Rice plant | Herbicidal activity | | |
|---|---|---|---|---|---|
| | | | Barnyard grass | Broadleaved weeds | Nutsedge |
| 136 | 20 | 5 | 4 | 5 | 5 |
| | 10 | 5 | 3 | 5 | 5 |
| 138 | 20 | 5 | 4 | 5 | 5 |
| | 10 | 5 | 4 | 5 | 5 |
| 140 | 20 | 5 | 4 | 5 | 5 |
| | 10 | 5 | 4 | 5 | 5 |
| 141 | 40 | 5 | 4 | 5 | 5 |
| | 20 | 5 | 3 | 5 | 5 |
| 142 | 20 | 5 | 4 | 5 | 5 |
| | 10 | 5 | 4 | 5 | 5 |
| 144 | 40 | 5 | 4 | 5 | 5 |
| | 10 | 5 | 3 | 5 | 5 |
| Control compound (a) | 20 | 4 | 2 | 5 | 5 |
| | 10 | 5 | 2 | 5 | 4 |
| | 5 | 5 | 1 | 3 | 3 |
| MCP | 20 | 2 | 4 | 5 | 5 |
| | 10 | 3 | 3 | 5 | 5 |
| | 5 | 3 | 2 | 5 | 5 |

EXAMPLE 14 (HERBICIDAL ACTIVITY BY POST-EMERGENCE TREATMENT)

Plastic trays (35×25×10 cm (in depth)) were filled with upland soil, and seeds of cocklebur, radish, redroot pigweed, common lambsquarters, black nightshade, sunflower, annual morningglory, large crabgrass, green foxtail and barnyard grass were sowed in the trays and grown for 2 to 3 weeks in a greenhouse. A required amount of the test compound was sprayed on the foliage of the test plants over the top by means of a small hand sprayer. After this foliar application, the plants were grown for an additional 3 weeks in the greenhouse. The herbicidal activity was then examined. At the above-described foliar application, the test compounds were each formulated into an emulsifiable concentrate and dispersed in water for application at a spray volume of 5 liters per are with addition of a wetting agent. The height of the plants at the foliar application varied depending upon the species, but they were at the 2- to 4-leaf stage and 2 to 10 cm high.

The results are shown in Table 2.

TABLE 2

| Compound No. | Dosage (weight of active ingredient, g/are) | Herbicidal activity | | | | | | | | | |
|---|---|---|---|---|---|---|---|---|---|---|---|
| | | Cocklebur | Radish | Redroot pigweed | Common lambsquarters | Black nightshade | Sunflower | Annual morningglory | Large crabgrass | Green foxtail | Barnyard grass |
| 1 | 10 | 5 | 5 | 5 | 5 | 5 | 5 | 5 | 5 | 5 | 5 |
| | 5 | 5 | 5 | 5 | 5 | 5 | 5 | 5 | 4 | 4 | 5 |
| | 2.5 | 5 | 5 | 5 | 5 | 5 | 5 | 5 | 3 | 4 | 4 |
| 2 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 5 | 4 | 4 |
| 3 | 10 | 5 | 5 | 5 | 5 | 5 | 5 | 5 | 4 | 5 | 5 |
| | 5 | 5 | 5 | 5 | 5 | 5 | 5 | 5 | 4 | 5 | 5 |
| | 2.5 | 5 | 5 | 5 | 5 | 5 | 5 | 5 | 3 | 3 | 3 |
| 4 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 5 | 3 | 5 | 4 |
| 5 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| | 5 | 5 | 5 | 5 | 5 | 5 | 5 | 5 | 3 | 5 | 4 |
| 6 | 10 | 5 | 5 | 5 | 5 | 5 | 5 | 5 | 5 | 5 | 5 |
| | 5 | 5 | 5 | 5 | 5 | 5 | 5 | 5 | 4 | 5 | 5 |
| | 2.5 | 5 | 5 | 5 | 5 | 5 | 5 | 5 | 3 | 5 | 4 |
| 7 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 3 | 3 | 4 |
| 8 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 4 | 5 | 4 |
| 9 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| | 5 | 5 | 5 | 5 | 5 | 5 | 5 | 5 | 4 | 5 | 4 |
| 10 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 5 | 4 | 5 | 4 |
| 11 | 10 | 5 | 5 | 5 | 5 | 5 | 5 | 5 | 4 | 5 | 5 |
| | 5 | 5 | 5 | 5 | 5 | 5 | 5 | 5 | 4 | 5 | 4 |
| | 2.5 | 5 | 5 | 5 | 5 | 5 | 5 | 5 | 3 | 5 | 4 |
| 12 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 4 | 5 | 5 | 4 |
| 13 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| | 5 | 5 | 5 | 5 | 5 | 5 | 5 | 5 | 4 | 5 | 4 |
| 14 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| | 5 | 5 | 5 | 5 | 5 | 5 | 5 | 5 | 4 | 4 | 4 |
| 15 | 20 | 5 | 5 | 5 | 5 | 5 | 5 | 5 | 5 | 5 | 4 |
| | 10 | 5 | 5 | 5 | 5 | 5 | 5 | 5 | 5 | 4 | 4 |
| | 5 | 5 | 5 | 5 | 5 | 5 | 5 | 5 | 3 | 3 | 3 |
| 16 | 20 | 5 | 5 | 5 | 5 | 5 | 5 | 5 | 4 | 4 | 4 |
| | 10 | 5 | 5 | 5 | 5 | 5 | 5 | 5 | 5 | 3 | 3 |
| | 5 | 5 | 5 | 5 | 5 | 5 | 5 | 5 | 3 | 3 | 3 |

TABLE 2-continued

| Compound No. | Dosage (weight of active ingredient, g/are) | Herbicidal activity | | | | | | | | |
|---|---|---|---|---|---|---|---|---|---|---|
| | | Cocklebur | Radish | Redroot pigweed | Common lambsquarters | Black nightshade | Sunflower | Annual morningglory | Large crabgrass | Green foxtail | Barnyard grass |
| 17 | 20 | 5 | 5 | 5 | 5 | 5 | 5 | 5 | 4 | 5 | 4 |
| | 10 | 5 | 5 | 5 | 5 | 5 | 5 | 5 | 3 | 4 | 4 |
| | 5 | 5 | 4 | 5 | 5 | 5 | 5 | 5 | 3 | 4 | 3 |
| 18 | 40 | 5 | 5 | 5 | 5 | 5 | 5 | 5 | 4 | 4 | 5 |
| | 20 | 5 | 5 | 5 | 5 | 5 | 5 | 5 | 4 | 3 | 5 |
| | 10 | 5 | 5 | 4 | 5 | 5 | 5 | 5 | 3 | 3 | 4 |
| 19 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| | 5 | 5 | 5 | 5 | 5 | 5 | 5 | 5 | 4 | 5 | 4 |
| 20 | 20 | 5 | 5 | 5 | 5 | 5 | 5 | 5 | 5 | 5 | 4 |
| | 10 | 5 | 5 | 5 | 5 | 5 | 5 | 5 | 4 | 4 | 4 |
| | 5 | 5 | 5 | 5 | 5 | 5 | 5 | 5 | 3 | 2 | 3 |
| 21 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| | 5 | 5 | 5 | 5 | 5 | 5 | 5 | 5 | 3 | 5 | 5 |
| 22 | 20 | 5 | 5 | 5 | 5 | 5 | 5 | 5 | 5 | 5 | 5 |
| | 10 | 5 | 5 | 5 | 5 | 5 | 5 | 5 | 4 | 3 | 5 |
| | 5 | 5 | 5 | 5 | 5 | 5 | 5 | 5 | 3 | 3 | 3 |
| 23 | 20 | 5 | 5 | 5 | 5 | 5 | 5 | 5 | 4 | 5 | 5 |
| | 10 | 5 | 5 | 5 | 5 | 5 | 5 | 5 | 4 | 5 | 5 |
| | 5 | 5 | 5 | 5 | 5 | 5 | 5 | 5 | 3 | 3 | 4 |
| 24 | 40 | 5 | 5 | 5 | 5 | 5 | 5 | 5 | 5 | 4 | 5 |
| | 20 | 5 | 5 | 5 | 5 | 5 | 5 | 5 | 3 | 4 | 4 |
| | 10 | 5 | 5 | 5 | 5 | 5 | 5 | 5 | 3 | 3 | 3 |
| 25 | 20 | 5 | 5 | 5 | 5 | 5 | 5 | 5 | 4 | 5 | 4 |
| | 10 | 5 | 5 | 5 | 5 | 4 | 5 | 5 | 4 | 5 | 3 |
| | 5 | 5 | 4 | 5 | 5 | 4 | 5 | 5 | 3 | 4 | 3 |
| 26 | 20 | 5 | 5 | 5 | 5 | 5 | 5 | 5 | 4 | 4 | 4 |
| | 10 | 4 | 5 | 4 | 5 | 5 | 5 | 5 | 4 | 3 | 3 |
| | 5 | 4 | 5 | 4 | 5 | 5 | 5 | 5 | 3 | 3 | 3 |
| 27 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| | 5 | 5 | 5 | 5 | 5 | 5 | 5 | 5 | 3 | 4 | 4 |
| 28 | 20 | 5 | 5 | 5 | 5 | 5 | 5 | 5 | 4 | 5 | 5 |
| | 10 | 5 | 5 | 5 | 5 | 5 | 5 | 5 | 4 | 5 | 4 |
| | 5 | 5 | 5 | 5 | 5 | 5 | 5 | 3 | 4 | 4 | |
| 29 | 20 | 5 | 5 | 5 | 5 | 5 | 5 | 5 | 5 | 5 | 5 |
| | 10 | 5 | 5 | 5 | 5 | 5 | 5 | 5 | 4 | 3 | 4 |
| | 5 | 5 | 5 | 4 | 5 | 4 | 5 | 5 | 3 | 3 | 4 |
| 30 | 20 | 5 | 5 | 5 | 5 | 5 | 5 | 5 | 4 | 5 | 5 |
| | 10 | 5 | 5 | 5 | 5 | 5 | 5 | 5 | 3 | 5 | 4 |
| | 5 | 5 | 5 | 5 | 5 | 5 | 5 | 5 | 3 | 4 | 3 |
| 31 | 20 | 5 | 5 | 5 | 5 | 5 | 5 | 5 | 4 | 5 | 5 |
| | 10 | 5 | 5 | 5 | 5 | 5 | 5 | 5 | 3 | 4 | 4 |
| | 5 | 5 | 5 | 5 | 5 | 5 | 5 | 5 | 3 | 3 | 3 |
| 32 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 3 |
| | 5 | 5 | 5 | 5 | 5 | 5 | 5 | 5 | 2 | 3 | 3 |
| 33 | 20 | 5 | 5 | 5 | 5 | 5 | 5 | 5 | 3 | 5 | 4 |
| | 10 | 5 | 5 | 5 | 5 | 5 | 5 | 5 | 3 | 3 | 4 |
| | 5 | 5 | 5 | 5 | 5 | 5 | 5 | 5 | 2 | 2 | 3 |
| 34 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 35 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 36 | 40 | 5 | 5 | 5 | 5 | 5 | 5 | 5 | 5 | 5 | 5 |
| | 20 | 5 | 5 | 5 | 5 | 5 | 5 | 5 | 4 | 4 | 4 |
| 37 | 40 | 5 | 5 | 5 | 5 | 5 | 5 | 5 | 5 | 5 | 5 |
| | 20 | 5 | 5 | 5 | 5 | 5 | 5 | 5 | 4 | 5 | 4 |
| 38 | 40 | 5 | 5 | 5 | 5 | 5 | 5 | 5 | 4 | 4 | 5 |
| | 20 | 5 | 5 | 5 | 5 | 5 | 5 | 5 | 4 | 4 | 4 |
| 39 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 40 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 41 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| 42 | 40 | 5 | 5 | 5 | 5 | 5 | 5 | 5 | 5 | 5 | 5 |
| | 20 | 5 | 5 | 5 | 5 | 5 | 5 | 5 | 5 | 4 | 4 |
| 43 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 44 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 45 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 46 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |

TABLE 2-continued

| Compound No. | Dosage (weight of active ingredient, g/are) | Herbicidal activity |||||||||
|---|---|---|---|---|---|---|---|---|---|---|
| | | Cocklebur | Radish | Redroot pigweed | Common lambs-quarters | Black night-shade | Sun-flower | Annual morning-glory | Large crab-grass | Green foxtail | Barnyard grass |
| 47 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 48 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 49 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 50 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 51 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 52 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 53 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 54 | 20 | 5 | 5 | 5 | 5 | 5 | 5 | 5 | 5 | 5 | 4 |
| | 10 | 5 | 5 | 5 | 5 | 5 | 5 | 5 | 4 | 4 | 4 |
| 55 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 56 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 57 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 58 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 59 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 60 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| 61 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 62 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 63 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 64 | 40 | 5 | 5 | 5 | 5 | 5 | 5 | 5 | 5 | 5 | 5 |
| | 20 | 5 | 5 | 5 | 5 | 5 | 5 | 5 | 4 | 4 | 4 |
| 65 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| 66 | 40 | 5 | 5 | 5 | 5 | 5 | 5 | 5 | 5 | 5 | 5 |
| | 20 | 5 | 5 | 5 | 5 | 5 | 5 | 5 | 4 | 4 | 4 |
| 67 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 69 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 70 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 71 | 40 | 5 | 5 | 5 | 5 | 5 | 5 | 5 | 5 | 5 | 5 |
| | 20 | 5 | 5 | 5 | 5 | 5 | 5 | 5 | 4 | 3 | 4 |
| 73 | 20 | 5 | 5 | 5 | 5 | 5 | 5 | 5 | 5 | 5 | |
| | 10 | 5 | 5 | 5 | 5 | 5 | 5 | 5 | 5 | 4 | 5 |
| 74 | 40 | 5 | 5 | 5 | 5 | 5 | 5 | 5 | 5 | 4 | 5 |
| | 20 | 5 | 5 | 5 | 5 | 5 | 5 | 5 | 3 | 4 | 4 |
| 75 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 76 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 77 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 79 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 81 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 82 | 20 | 5 | 5 | 5 | 5 | 5 | 5 | 5 | 5 | 4 | 5 |
| | 10 | 5 | 5 | 5 | 5 | 5 | 5 | 5 | 4 | 4 | 3 |
| 83 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 85 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 86 | 20 | 5 | 5 | 5 | 5 | 5 | 5 | 5 | 4 | 5 | 5 |
| 87 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 89 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 91 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 93 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |

TABLE 2-continued

| Compound No. | Dosage (weight of active ingredient, g/are) | Herbicidal activity | | | | | | | | |
|---|---|---|---|---|---|---|---|---|---|---|
| | | Cocklebur | Radish | Redroot pigweed | Common lambsquarters | Black nightshade | Sunflower | Annual morningglory | Large crabgrass | Green foxtail | Barnyard grass |
| 94 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 95 | 40 | 5 | 5 | 5 | 5 | 5 | 5 | 5 | 5 | 5 | 5 |
| | 20 | 5 | 5 | 5 | 5 | 5 | 5 | 5 | 4 | 5 | 4 |
| 96 | 40 | 5 | 5 | 5 | 5 | 5 | 5 | 5 | 5 | 5 | 5 |
| | 20 | 5 | 5 | 5 | 5 | 5 | 5 | 5 | 4 | 4 | 4 |
| 97 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| 99 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 100 | 40 | 5 | 5 | 5 | 5 | 5 | 5 | 5 | 5 | 5 | 5 |
| | 20 | 5 | 5 | 5 | 5 | 5 | 5 | 5 | 4 | 5 | 4 |
| 101 | 20 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| 102 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 103 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 4 |
| 105 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 3 |
| 106 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 4 |
| 107 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 108 | 40 | 5 | 5 | 5 | 5 | 5 | 5 | 5 | 5 | 5 | 4 |
| | 20 | 5 | 5 | 5 | 5 | 5 | 5 | 5 | 4 | 5 | 4 |
| 109 | 20 | 5 | 5 | 5 | 5 | 5 | 5 | 5 | 4 | 4 | 4 |
| | 10 | 5 | 5 | 5 | 5 | 5 | 5 | 5 | 3 | 4 | 3 |
| 113 | 20 | 5 | 5 | 5 | 5 | 5 | 5 | 5 | 5 | 5 | 4 |
| | 10 | 5 | 5 | 5 | 5 | 5 | 5 | 5 | 4 | 5 | 4 |
| 116 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 119 | 20 | 5 | 5 | 5 | 5 | 5 | 5 | 5 | 4 | 5 | 4 |
| | 10 | 5 | 5 | 5 | 5 | 5 | 5 | 5 | 4 | 3 | 3 |
| 121 | 20 | 5 | 5 | 5 | 5 | 5 | 5 | 5 | 4 | 4 | 4 |
| | 10 | 5 | 5 | 5 | 5 | 5 | 5 | 4 | 4 | 4 | 3 |
| 124 | 10 | 5 | 5 | 5 | 5 | 5 | 5 | 5 | 4 | 5 | 5 |
| | 5 | 5 | 5 | 5 | 5 | 5 | 5 | 5 | 4 | 4 | 4 |
| 125 | 20 | 5 | 5 | 5 | 5 | 5 | 5 | 5 | 5 | 4 | 4 |
| | 10 | 5 | 5 | 5 | 5 | 5 | 5 | 5 | 4 | 4 | 4 |
| 126 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 3 |
| 131 | 20 | 5 | 5 | 5 | 5 | 5 | 5 | 5 | 4 | 5 | 4 |
| | 10 | 5 | 5 | 5 | 5 | 5 | 5 | 5 | 3 | 4 | 4 |
| 132 | 20 | 5 | 5 | 5 | 5 | 5 | 5 | 5 | 4 | 5 | 4 |
| | 10 | 5 | 5 | 5 | 5 | 5 | 5 | 5 | 4 | 4 | 4 |
| 134 | 10 | 5 | 5 | 5 | 5 | 5 | 5 | 5 | 5 | 4 | 5 |
| | 5 | 5 | 5 | 5 | 5 | 5 | 5 | 5 | 4 | 4 | 3 |
| 135 | 20 | 5 | 5 | 5 | 5 | 5 | 5 | 5 | 4 | 5 | 5 |
| | 10 | 5 | 5 | 5 | 5 | 5 | 5 | 5 | 4 | 3 | 4 |
| 138 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 5 |
| 140 | 20 | 5 | 5 | 5 | 5 | 5 | 5 | 5 | 4 | 5 | 4 |
| | 10 | 5 | 5 | 5 | 5 | 5 | 5 | 5 | 3 | 4 | 3 |
| 142 | 20 | 5 | 5 | 5 | 5 | 5 | 5 | 5 | 5 | 4 | 4 |
| | 10 | 5 | 5 | 5 | 5 | 5 | 5 | 5 | 3 | 4 | 4 |
| Control compound (a) | 40 | 4 | 5 | 5 | 5 | 5 | 5 | 4 | 4 | 5 | 4 |
| | 20 | 4 | 4 | 4 | 5 | 5 | 5 | 3 | 3 | 3 | 2 |
| | 10 | 3 | 4 | 4 | 5 | 4 | 5 | 1 | 1 | 2 | 2 |
| Chloroxuron | 20 | 5 | 5 | 5 | 5 | 5 | 5 | 5 | 4 | 4 | 3 |
| | 10 | 5 | 5 | 5 | 5 | 5 | 5 | 5 | 2 | 3 | 3 |
| | 5 | 4 | 5 | 5 | 5 | 5 | 5 | 4 | 1 | 2 | 1 |
| Bentazon | 20 | 5 | 5 | 3 | 5 | 5 | 5 | 4 | 1 | 0 | 2 |
| | 10 | 5 | 5 | 2 | 5 | 5 | 5 | 2 | 0 | 0 | 1 |
| | 5 | 5 | 5 | 1 | 4 | 4 | 5 | 1 | 0 | 0 | 0 |

EXAMPLE 15 (SELECTIVITY OF CROP PLANTS BY POST-EMERGENCE TREATMENT)

Wagner's pots (1/5000 are) were each filled with upland soil, and the seeds of corn, wheat, rice plant, cotton, soybean and sugarbeet were separately sowed in the pots and grown for 2 to 3 weeks in a greenhouse. Thereafter, a required amount of the test compound was sprayed on the foliage of the test plants over the top by means of a small hand sprayer. After the spraying, the test plants were grown for an additional 3 weeks in the greenhouse, and the phototoxicity to each plant was then examined. At the above-described foliar application, the test compounds were each formulated into an emulsifiable concentrate and dispersed in water for application at a volume of 5 liters per are with addition of a wetting agent. At this foliar application, corn was in the 2-leaf stage, wheat in the 2-leaf stage, rice plant in the 3-leaf stage, cotton in the 1-leaf stage, soybean in the second trifoliate stage and sugarbeet in the 2-leaf stage. The results are shown in Table 3.

TABLE 3

| Compound No. | Dosage (weight of active ingredient, g/are) | Phytotoxicity | | | | | |
|---|---|---|---|---|---|---|---|
| | | Corn | Wheat | Rice plant | Cotton | Soybean | Sugarbeet |
| 1 | 20 | 3 | — | — | — | 4 | — |
| | 10 | 4 | — | — | — | 5 | — |
| | 5 | 5 | — | — | — | 5 | — |
| 2 | 20 | — | — | — | — | 4 | — |
| | 10 | — | — | — | — | 5 | — |
| | 5 | — | — | — | — | 5 | — |
| 3 | 10 | — | — | — | — | 4 | — |
| | 5 | — | — | — | — | — | 4 |
| | 2.5 | — | — | — | — | — | 5 |
| 7 | 20 | — | 4 | — | 3 | — | — |
| | 10 | — | 5 | — | 4 | — | — |
| | 5 | — | 5 | — | 5 | — | — |
| 12 | 20 | — | 5 | — | — | 4 | — |
| | 10 | — | 5 | — | — | 5 | — |
| | 5 | — | 5 | — | — | 5 | — |
| 13 | 20 | — | 3 | — | — | 4 | — |
| | 10 | — | 4 | — | — | 4 | — |
| | 5 | — | 4 | — | — | 5 | — |
| 16 | 20 | 3 | — | — | — | 4 | — |
| | 10 | 4 | — | — | — | 5 | — |
| | 5 | 4 | — | — | — | 5 | — |
| 17 | 20 | — | 3 | — | 4 | — | — |
| | 10 | — | 5 | — | 4 | — | — |
| | 5 | — | 5 | — | 5 | — | — |
| 20 | 20 | 3 | 4 | — | 4 | — | — |
| | 10 | 4 | 5 | — | 4 | — | — |
| | 5 | 5 | 5 | — | 5 | — | — |
| 22 | 20 | — | 4 | — | — | — | — |
| | 10 | — | 5 | — | — | — | — |
| | 5 | — | 5 | — | — | — | — |
| 25 | 20 | — | 5 | — | — | 4 | — |
| | 10 | — | 5 | — | — | 5 | — |
| | 5 | — | 5 | — | — | 5 | — |
| 34 | 20 | — | — | — | 4 | 4 | — |
| | 10 | — | — | — | 5 | 4 | — |
| 35 | 20 | — | 4 | 5 | 4 | 4 | — |
| | 10 | — | 5 | 5 | 5 | 5 | — |
| 36 | 40 | 5 | — | 5 | — | — | 4 |
| | 20 | 5 | — | 5 | — | — | 5 |
| 37 | 40 | 4 | — | — | — | 4 | — |
| | 20 | 5 | — | — | — | 4 | — |
| 40 | 20 | — | 4 | — | 4 | 5 | 4 |
| | 10 | — | 5 | — | 5 | 5 | 5 |
| 41 | 20 | 5 | — | 4 | — | 4 | 4 |
| | 10 | 5 | — | 5 | — | 5 | 4 |
| 44 | 20 | — | — | 4 | — | — | — |
| | 10 | — | — | 5 | — | — | — |
| 45 | 20 | — | — | 4 | — | — | — |
| | 10 | — | — | 5 | — | — | — |
| 48 | 20 | 4 | 4 | — | — | 5 | 4 |
| | 10 | 5 | 5 | — | — | 5 | 5 |
| 49 | 20 | — | — | 5 | — | — | — |
| | 10 | — | — | 5 | — | — | — |
| 50 | 20 | — | 5 | 4 | — | — | 4 |
| | 10 | — | 5 | 5 | — | — | 4 |
| 54 | 20 | — | — | — | — | 5 | — |
| | 10 | — | — | — | — | 5 | — |
| 56 | 20 | — | — | 5 | — | 4 | — |
| | 10 | — | — | 5 | — | 5 | — |
| 58 | 20 | — | — | — | — | 4 | — |
| | 10 | — | — | — | — | 5 | — |
| 60 | 20 | 4 | — | — | — | — | — |
| | 10 | 5 | — | — | — | — | — |

TABLE 3-continued

| Compound No. | Dosage (weight of active ingredient, g/are) | Phytotoxicity | | | | | |
|---|---|---|---|---|---|---|---|
| | | Corn | Wheat | Rice plant | Cotton | Soybean | Sugarbeet |
| 62 | 20 | — | — | — | — | 4 | — |
| | 10 | — | — | — | — | 4 | — |
| 65 | 20 | — | — | 5 | — | — | — |
| | 10 | — | — | 5 | — | — | — |
| 66 | 40 | 5 | 5 | — | 4 | 5 | — |
| | 20 | 5 | 5 | — | 5 | 5 | — |
| 69 | 20 | — | 4 | — | — | — | — |
| | 10 | — | 5 | — | — | — | — |
| 70 | 20 | — | 4 | — | — | — | 4 |
| | 10 | — | 5 | — | — | — | 4 |
| 73 | 20 | 4 | — | — | — | — | — |
| | 10 | 4 | — | — | — | — | — |
| 74 | 40 | — | — | — | 5 | 4 | — |
| | 20 | — | — | — | 5 | 5 | — |
| 95 | 40 | — | — | 5 | 4 | 4 | — |
| | 20 | — | — | 5 | 5 | 5 | — |
| 99 | 20 | — | — | 4 | — | — | — |
| | 10 | — | — | 5 | — | — | — |
| 109 | 20 | — | — | — | 5 | 4 | — |
| | 10 | — | — | — | 5 | 5 | — |
| 116 | 20 | 4 | — | — | — | — | 4 |
| | 10 | 5 | — | — | — | — | 5 |
| 121 | 20 | — | 5 | 5 | — | — | — |
| | 10 | — | 5 | 5 | — | — | — |
| 125 | 20 | — | — | — | — | 4 | — |
| | 10 | — | — | — | — | 5 | — |
| 126 | 20 | — | — | — | — | 4 | — |
| | 10 | — | — | — | — | 5 | — |
| 135 | 20 | — | — | — | — | 5 | — |
| | 10 | — | — | — | — | 5 | — |
| Diuron | 20 | 0 | 0 | — | 0 | 0 | 0 |
| | 10 | 1 | 0 | — | 0 | 0 | 0 |
| | 5 | 3 | 1 | — | 2 | 0 | 0 |
| Atrazine | 20 | 4 | — | — | — | — | — |
| | 10 | 4 | — | — | — | — | — |
| | 5 | 5 | — | — | — | — | — |
| Barban | 20 | — | 3 | — | — | — | — |
| | 10 | — | 3 | — | — | — | — |
| | 5 | — | 4 | — | — | — | — |
| Fluometuron | 20 | — | — | — | 3 | — | — |
| | 10 | — | — | — | 4 | — | — |
| | 5 | — | — | — | 5 | — | — |
| Chloroxuron | 20 | — | — | — | — | 3 | — |
| | 10 | — | — | — | — | 4 | — |
| | 5 | — | — | — | — | 4 | — |
| Bentazon | 20 | 4 | — | — | — | 4 | — |
| | 10 | 4 | — | — | — | 5 | — |
| | 5 | 5 | — | — | — | 5 | — |

EXAMPLE 16 (PRE-EMERGENCE TREATMENT)

Plastic trays (35×25×10 cm (in depth)) were filled with upland soil, and the seeds of soybean, cotton, sugarbeet, corn, wheat, rice plant, redroot pigweed, common lambsquarters, radish, common purslane and large crabgrass were separately sowed in the trays. A required amount of the wettable power of each test compound was dispersed in water for application at a volume of 3 liters per are are sprayed to the whole surface of the soil by means of a small hand sprayer. After the spraying, the test plants were grown in a greenhouse for 20 days, and the phytotoxicity and the herbicidal activity were examined. The examination was carried out by the same criteria as described above. The results are shown in Table 4.

TABLE 4

| Compound No. | Dosage (weight of active ingredient g/are) | Phytotoxicity | | | | | | Herbicidal activity | | | | |
|---|---|---|---|---|---|---|---|---|---|---|---|---|
| | | Soybean | Cotton | Sugar-beet | Corn | Wheat | Rice plant | Redroot pigweed | Common lambs-quarters | Radish | Common purslane | Large crab-grass |
| 1 | 40 | 5 | 5 | 5 | 5 | 5 | 5 | 5 | 5 | 5 | 5 | 3 |
| | 20 | 5 | 5 | 5 | 5 | 5 | 5 | 5 | 4 | 5 | 5 | 2 |
| 2 | 40 | 5 | 5 | 5 | 5 | 5 | 5 | 5 | 5 | 5 | 5 | 2 |
| | 20 | 5 | 5 | 5 | 5 | 5 | 5 | 5 | 4 | 4 | 5 | 1 |
| 4 | 40 | 5 | 5 | 5 | 5 | 5 | 5 | 5 | 5 | 4 | 5 | 2 |
| | 20 | 5 | 5 | 5 | 5 | 5 | 5 | 5 | 4 | 4 | 5 | 0 |
| 8 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 5 | 5 | 3 |
| 10 | 40 | 5 | 5 | 5 | 5 | 5 | 5 | 5 | 5 | 4 | 5 | 3 |
| | 20 | 5 | 5 | 5 | 5 | 5 | 5 | 5 | 5 | 4 | 5 | 2 |
| 14 | 40 | 5 | 5 | 5 | 5 | 5 | 5 | 5 | 5 | 4 | 5 | 3 |
| | 20 | 5 | 5 | 5 | 5 | 5 | 5 | 5 | 5 | 2 | 5 | 2 |
| 16 | 40 | 5 | 5 | 5 | 5 | 5 | 5 | 5 | 5 | 3 | 5 | 3 |
| | 20 | 5 | 5 | 5 | 5 | 5 | 5 | 5 | 4 | 3 | 5 | 1 |
| 20 | 40 | 5 | 5 | 5 | 5 | 5 | 5 | 5 | 5 | 4 | 5 | 3 |
| | 20 | 5 | 5 | 5 | 5 | 5 | 5 | 5 | 5 | 4 | 5 | 2 |
| 26 | 40 | 5 | 5 | 5 | 5 | 5 | 5 | 5 | 5 | 3 | 5 | 2 |
| | 20 | 5 | 5 | 5 | 5 | 5 | 5 | 5 | 4 | 2 | 4 | 1 |
| 28 | 40 | 5 | 5 | 5 | 5 | 5 | 5 | 4 | 5 | 4 | 5 | 3 |
| | 20 | 5 | 5 | 5 | 5 | 5 | 5 | 4 | 4 | 2 | 5 | 1 |
| 34 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 4 |
| 35 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 5 | 5 | 4 |
| 37 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 5 | 5 | 4 |
| 40 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 43 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 46 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 47 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 49 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 4 |
| 51 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 52 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 53 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 58 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 62 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 65 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 4 |
| 70 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 73 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 83 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 5 | 5 | 4 |
| 87 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 99 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 4 |
| 113 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 4 |
| 116 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 5 | 5 | 4 |
| 121 | 40 | 5 | 5 | 5 | 5 | 5 | 5 | 5 | 5 | 5 | 5 | 4 |
| | 20 | 5 | 5 | 5 | 5 | 5 | 5 | 5 | 5 | 4 | 5 | 4 |
| 124 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| 134 | 40 | 5 | 5 | 5 | 5 | 5 | 5 | 5 | 5 | 5 | 5 | 5 |
| | 20 | 5 | 5 | 5 | 5 | 5 | 5 | 5 | 5 | 5 | 5 | 5 |
| Chloramben | 20 | 5 | 1 | — | 2 | 4 | — | 2 | 2 | 0 | 5 | 3 |
| | 10 | 5 | 2 | — | 3 | 5 | — | 2 | 1 | 0 | 5 | 2 |
| Diuron | 20 | 0 | 2 | 0 | 1 | 0 | — | 5 | 5 | 5 | 5 | 4 |
| | 10 | 1 | 4 | 0 | 3 | 1 | — | 5 | 5 | 5 | 5 | 3 |

The application of the compounds (I) as fungicides will be illustrated in the following Example wherein a commercially available fungicide known under the ge-

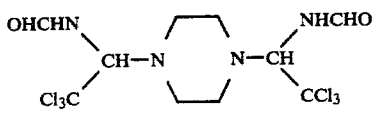

EXAMPLE 17 (PROTECTIVE EFFECT ON LEAF RUST OF WHEAT)

Wheats (var.: Nohrin No. 61) were grown up to the one-leaf stage in a flower pot of 9 cm in diameter, inoculated with *Puccinia recondita* and placed under a humid chamber for 18 hours. Then, each of the emulsifiable concentrates containing the test compounds was diluted with water and sprayed on the test plants in a rate of 15 ml/pot. The test plants were placed in a chamber kept at 20° C. and grown under a fluorescent lamp for an additional 10 days. The infection state was observed, and the disease severity was calculated on the basis of the following standard:

| Disease index | Infection state |
|---|---|
| 0 | No infectious spot on the examined leaf |
| 1 | Less than 10 infectious spots on the examined leaf |
| 2 | 11–20 infectious spots on the examined leaf |
| 4 | 21–50 infectious spots on the examined leaf |
| 8 | More than 51 infectious spots on the examined leaf |

$$\text{Disease severity (\%)} = \frac{\Sigma(\text{Disease index}) \times (\text{Number of leaves})}{8 \times (\text{Total number of leaves examined})} \times 100$$

The results are shown in Table 5.

TABLE 5

| Compound No. | Concentration of active ingredient (ppm) | Disease severity (%) |
|---|---|---|
| 1 | 200 | 0.0 |
| 3 | 200 | 0.0 |
| 4 | 200 | 0.0 |
| 5 | 200 | 5.1 |
| 10 | 200 | 9.6 |
| 14 | 200 | 10.3 |
| 24 | 200 | 0.0 |
| 27 | 200 | 0.4 |
| 32 | 200 | 0.0 |
| 35 | 200 | 0.0 |
| 40 | 200 | 7.5 |
| 43 | 200 | 0.0 |
| 49 | 200 | 2.0 |
| 53 | 200 | 2.5 |
| 65 | 200 | 1.2 |
| 75 | 200 | 0.0 |
| 87 | 200 | 7.2 |
| 88 | 200 | 0.0 |
| 100 | 200 | 3.3 |
| 110 | 200 | 10.0 |
| 128 | 200 | 2.0 |
| 134 | 200 | 0.0 |
| Trisorine | 200 | 15.1 |

What is claimed is:

1. A herbicidal composition comprising as an active ingredient at least one of the following compounds of the formula:

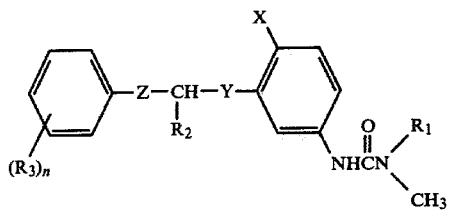

wherein $R_1$ is hydrogen, methyl or methoxy, $R_2$ is hydrogen or lower alkyl, $R_3$, which may be the same or different, is halogen, lower alkyl, lower alkoxy, lower alkylthio or trifluoromethyl, n is an integer of 0 to 5, X is hydrogen or halogen, Y is oxygen or sulfur and Z is a straight or branched $C_1$–$C_8$ alkylene group which may optionally have at least one atom of oxygen and/or sulfur at the end of and/or inside the carbon chain, and an inert carrier.

2. The composition according to claim 1, wherein the concentration of the active ingredient is from about 1 to 80% by weight.

3. The composition according to claim 1, wherein $R_1$ is methyl or methoxy, $R_2$ is hydrogen, $R_3$, which may be the same or different, is halogen, lower alkyl, lower alkoxy, lower alkylthio or trifluoromethyl, n is an integer of 0 to 5, X is hydrogen, Y is oxygen and Z is methylene or ethylene.

4. The composition according to claim 1, wherein the compound is N'-3-phenethyloxyphenyl-N,N-dimethylurea.

5. The composition according to claim 1, wherein the compound is N'-3-[2-(2-methylphenyl)ethoxy]phenyl-N-methoxy-N-methylurea.

6. The composition according to claim 1, wherein the compound is N'-3-[2-(4-methylphenyl)ethoxy]phenyl-N,N-dimethylurea.

7. The composition according to claim 1, wherein the compound is N'-3-[3-(2-methylphenyl)propoxy]phenyl-N-methoxy-N-methylurea.

8. A method for controlling weeds which comprises applying an effective weed-controlling amount of at least one of the compounds of the formula:

wherein $R_1$ is hydrogen, methyl or methoxy, $R_2$ is hydrogen or lower alkyl, $R_3$, which may be the same or different, is halogen, lower alkyl, lower alkoxy, lower alkylthio or trifluoromethyl, n is an integer of 0 to 5, X is hydrogen or halogen, Y is oxygen or sulfur and Z is a straight or branched $C_1$–$C_8$ alkylene group which optionally may have at least one atom of oxygen and/or sulfur at the end of and/or inside the carbon chain, to the area where the weeds grow.

9. The method according to claim 8, wherein the application is effected by post-emergence treatment.

10. A method of selectively combating weeds in the cultivation of sugarbeets, soybeans, cotton, rice, wheat or corn, which comprises applying a herbicidally effective amount of at least one of the compounds of the formula:

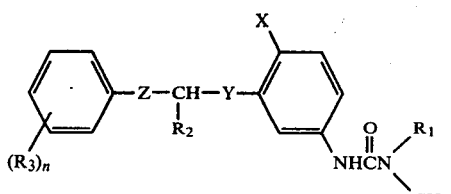

wherein $R_1$ is hydrogen, methyl or methoxy, $R_2$ is hydrogen or lower alkyl, $R_3$, which may be the same or different, is halogen, lower alkyl, lower alkoxy, lower alkylthio or trifluoromethyl, n is an integer of 0 to 5, X is hydrogen or halogen, Y is oxygen or sulfur and Z is a straight or branched $C_1$–$C_8$ alkylene group which may optionally have at least one atom of oxygen and/or sulfur at the end of and/or inside the carbon chain, to the area where the sugarbeet, soybean, cotton, rice, wheat or corn corp is cultivated.

11. The method according to claim 10, wherein the application is effected by post-emergence treatment.

* * * * *